US011591375B2

(12) United States Patent
Bermudez

(10) Patent No.: US 11,591,375 B2
(45) Date of Patent: Feb. 28, 2023

(54) **IMMUNOGENIC COMPOSITIONS COMPRISING *MYCOBACTERIUM BOVIS* SURFACE PROTEINS AND USES THEREOF**

(71) Applicant: Oregon State University, Corvallis, OR (US)

(72) Inventor: Luiz E. Bermudez, Corvallis, OR (US)

(73) Assignee: Oregon State University, Corvallis, OR (US)

(*) Notice: Subject to any disclaimer, the term of this patent is extended or adjusted under 35 U.S.C. 154(b) by 0 days.

(21) Appl. No.: 16/963,770

(22) PCT Filed: Jan. 22, 2019

(86) PCT No.: PCT/US2019/014598
§ 371 (c)(1),
(2) Date: Jul. 21, 2020

(87) PCT Pub. No.: WO2019/144139
PCT Pub. Date: Jul. 25, 2019

(65) Prior Publication Data

US 2021/0040162 A1 Feb. 11, 2021

Related U.S. Application Data

(60) Provisional application No. 62/620,047, filed on Jan. 22, 2018.

(51) Int. Cl.

| | |
|---|---|
| ***C07K 14/35*** | (2006.01) |
| ***A61P 31/04*** | (2006.01) |
| ***A61K 9/00*** | (2006.01) |
| ***A61K 39/04*** | (2006.01) |
| ***A61K 39/00*** | (2006.01) |

(52) U.S. Cl.
CPC ............ *C07K 14/35* (2013.01); *A61K 9/0019* (2013.01); *A61K 39/04* (2013.01); *A61P 31/04* (2018.01); *A61K 2039/54* (2013.01); *A61K 2039/543* (2013.01); *A61K 2039/552* (2013.01)

(58) Field of Classification Search
CPC ....... C07K 14/35; A61P 31/04; A61K 9/0019; A61K 39/04; A61K 2039/54; A61K 2039/543; A61K 2039/552
See application file for complete search history.

(56) References Cited

U.S. PATENT DOCUMENTS

| | | | | |
|---|---|---|---|---|
| 5,330,754 A | 7/1994 | Kapoor et al. | | |
| 6,949,345 B1 * | 9/2005 | Menozzi | C07K 14/35 424/130.1 |
| 7,595,383 B1 * | 9/2009 | Gennaro | C07K 14/35 424/234.1 |
| 7,608,277 B2 * | 10/2009 | Roth | A61K 39/04 424/248.1 |
| 9,181,311 B2 * | 11/2015 | Spencer | A61P 31/06 |
| 9,339,534 B2 * | 5/2016 | Carroll | C07K 14/35 |
| 9,926,346 B2 * | 3/2018 | Fulkerson | A61K 49/0006 |
| 9,982,039 B2 * | 5/2018 | Carroll | A61K 39/04 |
| 11,021,534 B2 * | 6/2021 | Hall | G01N 33/5695 |
| 2002/0169308 A1 * | 11/2002 | Hillman | C07K 14/705 536/23.5 |
| 2007/0042383 A1 * | 2/2007 | Kapur | C12Q 1/689 435/6.15 |
| 2012/0034257 A1 | 2/2012 | Pethe et al. | |
| 2015/0291669 A1 * | 10/2015 | Fulkerson | A61K 49/0006 424/9.81 |
| 2021/0040162 A1 * | 2/2021 | Bermudez | A61P 31/04 |

FOREIGN PATENT DOCUMENTS

| | | | |
|---|---|---|---|
| CN | 106589082 | 4/2017 | |
| WO | WO-2006060484 A2 * | 6/2006 | A61K 39/04 |
| WO | WO-2008073444 A2 * | 6/2008 | A61P 31/00 |
| WO | WO-2009114139 A2 * | 9/2009 | A61K 45/06 |

OTHER PUBLICATIONS

Sechi et al Vaccine, 2006, 24:236-243. available online:Nov. 28, 2005 (Year: 2005).*
Chen et al, international Journal of microbolgy.2019, article ID 9167271, 12 pages. published: Jun. 3, 2019 (Year: 2019).*
Ellis (Vaccines, W.B. Saunders Company, Chapter 29, 1988, pp. 568-574).*
Skolnick et al. (Trends in Biotechnology 18: 34-39, 2000).*
Bowie et al (Science, 1990, 257:1306-1310).*
Colman Res. (Immunology, Jan. 1994, vol. 145, pp. 33-36).*
Greenspan et al. (Nature Biotechnology 7: 936-937, 1999).*
Boslego et al (Vaccines and Immunotherapy, 1991, Chapter 17).*
Chen et al., "*Mycobacterium bovis* BCG Surface Antigens Expressed under the Granuloma-Like Conditions as Potential Inducers of the Protective Immunity," *Int J Microbiol* 2019:9167271, 2019.
International Search Report and Written Opinion for PCT/US2019/014598, dated May 31, 2019.
McNamara et al., "Surface Proteome of '*Mycobacterium avium* subsp. *hominissuis*' during the Early Stages of Macrophage Infection," *Infect Immun* 80:1868-1880, 2012.

* cited by examiner

*Primary Examiner* — Robert A Zeman
(74) *Attorney, Agent, or Firm* — Klarquist Sparkman, LLP

(57) ABSTRACT

Antigenic surface proteins expressed by *Mycobacterium bovis* under conditions that mimic the natural environment in a host are described. Use of the identified surface proteins in immunogenic compositions for immunization against *M. bovis* are also described. Nucleic acid molecules and plasmids encoding the *M. bovis* surface proteins are further described.

18 Claims, 5 Drawing Sheets

Specification includes a Sequence Listing.

% Binding on A549 cells
0
2
4
6
8
10
**
30min
1h
Time point
Regular lab condition
Granuloma-like condition % Binding toTHP-1 cells
0.0
0.2
0.4
0.6
0.8
1.0
**
**
30min
1h
Time point
Regular lab condition
Granuloma-like condition % Invasion of A549 cells
0.0
0.5
1.0
1.5
2.0
2.5
3.0
*
*
30min
1h
Time point
Regular lab condition
Granuloma-like condition % Invasion of THP-1 cells
0.00
0.01
0.02
0.03
0.04
0.05
*
30min
1h
Time point
Regular lab condition
Granuloma-like condition

SEQUENCE LISTING

<160> NUMBER OF SEQ ID NOS: 24

<210> SEQ ID NO 1
<211> LENGTH: 1095
<212> TYPE: DNA
<213> ORGANISM: Mycobacterium bovis

<400> SEQUENCE: 1
gtgcaaggag ccgttgctgg tctggtgttt ctggccgtcc tggtgatttt cgccatcatc 60
gtggtggcca agtcggtggc gctgatcccg caggcggagg ccgcggtgat cgagcggctg 120
ggtcgctata gtcgtacggt cagtgggcag ttgacgctgt tggtgccgtt catcgaccgc 180
gtccgggctc gggtggacct gcgcgagcgg gtggtgtcgt ttccgccgca accggtgatc 240
accgaggaca acttgacgct gaacatcgac accgtcgtct acttccaggt gaccgttccg 300
caggcggcgg tgtacgagat cagcaattac atcgtcgggg tcgaacagct caccaccacc 360
accaccctgc gcaacgttgt cggcgggatg acgctggagc agacgttgac ctcgcgtgac 420
cagatcaacg cccagctgcg cggcgttctc gatgaggcga ccggccgctg ggtctgcgg 480 gtggcgcggg tggagctgcg cagcatcgat ccgccgccgt cgattcaggc gtcgatggaa 540
aagcagatga aggccgaccg ggagaagcga gcgatgattc tgaccgccga aggtacccgg 600
gaggcggcga taaaacaggc cgaggggcaa aagcaggcgc agatcctggc cgccgagggc 660
gccaagcagg ccgcgatctt ggctgctgag gccgatcggc agtctcggat gctgcgcgct 720
cagggtgagc gcgccgcggc ctacctgcag gcgcaaggc aggccaaggc catcgagaag 780
acgttcgccg cgatcaaggc tggccggccc accccggaga tgctggccta ccaatacctg 840
cagacgctgc cggagatggc gcgtggggac gccaacaagg tatgggtggt gcccagcgac 900
ttcaacgccg cactgcaggg ttcaccaggc tgctgggcaa gccgggtgag gacggggtgt 960
tccggttcga gccgtccccg gtcgaagacc agcccaagca cgcggccgac ggtgacgacg 1020
ccgaggtcgc cggctggttc tccaccgata ccgacccgtc gatcgctcgg gcggtggcta 1080
cagccgaggc gatag 1095

<210> SEQ ID NO 2
<211> LENGTH: 381
<212> TYPE: PRT
<213> ORGANISM: Mycobacterium bovis

<400> SEQUENCE: 2

Met Gln Gly Ala Val Ala Gly Leu Val Phe Leu Ala Val Leu Val Ile
1 5 10 15

Phe Ala Ile Ile Val Val Ala Lys Ser Val Ala Leu Ile Pro Gln Ala
20 25 30

Glu Ala Ala Val Ile Glu Arg Leu Gly Arg Tyr Ser Arg Thr Val Ser
35 40 45

Gly Gln Leu Thr Leu Leu Val Pro Phe Ile Asp Arg Val Arg Ala Arg
50 55 60

Val Asp Leu Arg Glu Arg Val Val Ser Phe Pro Pro Gln Pro Val Ile
65 70 75 80

Thr Glu Asp Asn Leu Thr Leu Asn Ile Asp Thr Val Val Tyr Phe Gln
85 90 95

Val Thr Val Pro Gln Ala Ala Val Tyr Glu Ile Ser Asn Tyr Ile Val
100 105 110

Gly Val Glu Gln Leu Thr Thr Thr Thr Leu Arg Asn Val Val Gly Gly
115 120 125

-continued

```
Met Thr Leu Glu Gln Thr Leu Thr Ser Arg Asp Gln Ile Asn Ala Gln
    130                 135                 140

Leu Arg Gly Val Leu Asp Glu Ala Thr Gly Arg Trp Gly Leu Arg Val
145                 150                 155                 160

Ala Arg Val Glu Leu Arg Ser Ile Asp Pro Pro Pro Ser Ile Gln Ala
                165                 170                 175

Ser Met Glu Lys Gln Met Lys Ala Asp Arg Glu Lys Arg Ala Met Ile
            180                 185                 190

Leu Thr Ala Glu Gly Thr Arg Glu Ala Ala Ile Lys Gln Ala Glu Gly
        195                 200                 205

Gln Lys Gln Ala Gln Ile Leu Ala Ala Glu Gly Ala Lys Gln Ala Ala
    210                 215                 220

Ile Leu Ala Ala Glu Ala Asp Arg Gln Ser Arg Met Leu Arg Ala Gln
225                 230                 235                 240

Gly Glu Arg Ala Ala Ala Tyr Leu Gln Ala Gln Gly Gln Ala Lys Ala
                245                 250                 255

Ile Glu Lys Thr Phe Ala Ala Ile Lys Ala Gly Arg Pro Thr Pro Glu
            260                 265                 270

Met Leu Ala Tyr Gln Tyr Leu Gln Thr Leu Pro Glu Met Ala Arg Gly
        275                 280                 285

Asp Ala Asn Lys Val Trp Val Val Pro Ser Asp Phe Asn Ala Ala Leu
    290                 295                 300

Gln Gly Phe Thr Arg Leu Leu Gly Lys Pro Gly Glu Asp Gly Val Phe
305                 310                 315                 320

Arg Phe Glu Pro Ser Pro Val Glu Asp Gln Pro Lys His Ala Ala Asp
                325                 330                 335

Gly Asp Asp Ala Glu Val Ala Gly Trp Phe Ser Thr Asp Thr Asp Pro
            340                 345                 350

Ser Ile Ala Arg Ala Val Ala Thr Ala Glu Ala Ile Ala Arg Lys Pro
        355                 360                 365

Val Glu Gly Ser Leu Gly Thr Pro Pro Arg Leu Thr Gln
    370                 375                 380
```

<210> SEQ ID NO 3
<211> LENGTH: 480
<212> TYPE: DNA
<213> ORGANISM: Mycobacterium bovis

<400> SEQUENCE: 3

```
gtggacacaa ctgtcgctac catgatcagc aaatacatac agataaccgt ttgctcttgg     60

agcccggtgg aggtcacatc gatgagcacg acgttcgctg cccgcctgaa ccgcctgttc    120

gacacggttt atccgcccgg acgcgggcca catacctccg cggaggtgat cgcggcgctc    180

aaggcagagg gcatcacgat gtcggctccc tacctatcac agctacgctc aggaaaccgt    240

acgaacccat cgggggcgac catggccgcc ctggccaact tcttccgcat caaggcggcc    300

tacttcaccg acgacgagta ctacgaaaag ctcgacaagg aattgcagtg gctgtgcacg    360

atgcgcgacg acggcgtgcg ccggatcgcg cagcgggccc acgggttgcc ctccgcggcg    420

cagcagaagg tgttggaccg gatcgacgag ctgcggcgtg ccgaagggat cgacgcttag    480
```

<210> SEQ ID NO 4
<211> LENGTH: 159
<212> TYPE: PRT
<213> ORGANISM: Mycobacterium bovis -continued

<400> SEQUENCE: 4

Met Asp Thr Thr Val Ala Thr Met Ile Ser Lys Tyr Ile Gln Ile Thr
1               5                   10                  15

Val Cys Ser Trp Ser Pro Val Glu Val Thr Ser Met Ser Thr Thr Phe
            20                  25                  30

Ala Ala Arg Leu Asn Arg Leu Phe Asp Thr Val Tyr Pro Pro Gly Arg
        35                  40                  45

Gly Pro His Thr Ser Ala Glu Val Ile Ala Ala Leu Lys Ala Glu Gly
    50                  55                  60

Ile Thr Met Ser Ala Pro Tyr Leu Ser Gln Leu Arg Ser Gly Asn Arg
65                  70                  75                  80

Thr Asn Pro Ser Gly Ala Thr Met Ala Ala Leu Ala Asn Phe Phe Arg
                85                  90                  95

Ile Lys Ala Ala Tyr Phe Thr Asp Asp Glu Tyr Tyr Glu Lys Leu Asp
            100                 105                 110

Lys Glu Leu Gln Trp Leu Cys Thr Met Arg Asp Asp Gly Val Arg Arg
        115                 120                 125

Ile Ala Gln Arg Ala His Gly Leu Pro Ser Ala Ala Gln Gln Lys Val
    130                 135                 140

Leu Asp Arg Ile Asp Glu Leu Arg Arg Ala Glu Gly Ile Asp Ala
145                 150                 155

<210> SEQ ID NO 5
<211> LENGTH: 666
<212> TYPE: DNA
<213> ORGANISM: Mycobacterium bovis

<400> SEQUENCE: 5
atgcggacgg tctatcacca gcggctaacc gagttggccg gacgattggg agagatgtgc 60
agcctggccg ggatagcgat gaaacgcgca acgcaggctc tgctcgaggc cgacattggc 120
gccgctgaac aagtaatccg tgaccatgag cggatcgtgg cgatgcgagc ccaagtcgaa 180
aaggaagcgt tcgcgctgct ggcgttgcaa catccggtgt ccggcgagct gcgggaaatc 240
ttcagtgcgg tgcagatcat cgccgacacc gagcgcatgg gtgcgttggc tgtgcatatt 300
gccaagatca cccgacgcga gtatccgaac caggtgcttc ctgaggaagt tcgcaactgc 360
ttcgccgaca tggcgaaggt ggcaatcgcg ttgggtgaca gtgcaagaca agtgctggtg 420
aaccgtgacc cgcaggaagc cgcgcaactg cacgatcgtg acgacgcgat ggatgacctg 480
cataggcatt tgctgagcgt gctgatagat cgagaatggc ggcacggcgt tcgcgtcggt 540
gtggaaacgg cgttgctggg tcgtttcttt gagcgcttcg ccgaccacgc tgtggaagtg 600
ggccgccgcg tcatcttcat ggtcaccggg gtgctaccga ccgaggacga gatttccact 660
tactga 666

<210> SEQ ID NO 6
<211> LENGTH: 221
<212> TYPE: PRT
<213> ORGANISM: Mycobacterium bovis

<400> SEQUENCE: 6

Met Arg Thr Val Tyr His Gln Arg Leu Thr Glu Leu Ala Gly Arg Leu
1               5                   10                  15

Gly Glu Met Cys Ser Leu Ala Gly Ile Ala Met Lys Arg Ala Thr Gln
            20                  25                  30

```
Ala Leu Leu Glu Ala Asp Ile Gly Ala Ala Glu Gln Val Ile Arg Asp
        35                  40                  45

His Glu Arg Ile Val Ala Met Arg Ala Gln Val Glu Lys Glu Ala Phe
    50                  55                  60

Ala Leu Leu Ala Leu Gln His Pro Val Ser Gly Glu Leu Arg Glu Ile
65                  70                  75                  80

Phe Ser Ala Val Gln Ile Ile Ala Asp Thr Glu Arg Met Gly Ala Leu
                85                  90                  95

Ala Val His Ile Ala Lys Ile Thr Arg Arg Glu Tyr Pro Asn Gln Val
            100                 105                 110

Leu Pro Glu Glu Val Arg Asn Cys Phe Ala Asp Met Ala Lys Val Ala
        115                 120                 125

Ile Ala Leu Gly Asp Ser Ala Arg Gln Val Leu Val Asn Arg Asp Pro
    130                 135                 140

Gln Glu Ala Ala Gln Leu His Asp Arg Asp Asp Ala Met Asp Asp Leu
145                 150                 155                 160

His Arg His Leu Leu Ser Val Leu Ile Asp Arg Glu Trp Arg His Gly
                165                 170                 175

Val Arg Val Gly Val Glu Thr Ala Leu Leu Gly Arg Phe Phe Glu Arg
            180                 185                 190

Phe Ala Asp His Ala Val Glu Val Gly Arg Arg Val Ile Phe Met Val
        195                 200                 205

Thr Gly Val Leu Pro Thr Glu Asp Glu Ile Ser Thr Tyr
    210                 215                 220
```

```
<210> SEQ ID NO 7
<211> LENGTH: 584
<212> TYPE: DNA
<213> ORGANISM: Mycobacterium bovis

<400> SEQUENCE: 7

atggctgaaa actcgaacat tgatgacatc aaggctccgt tgcttgccgc gcttggagcg      60

gccgacctgg ccttggccac tgtcaacgag ttgatcacga acctgcgtga gcgtgcggag     120

gagactcgta cggacacccg cagccgggtc gaggagagcc gtgctcgcct gaccaagctg     180

caggaagatc tgcccgagca gctcaccgag ctgcgtgaga agttcaccgc cgaggagctg     240

cgtaaggccg ccgagggcta cctcgaggcc gcgactagcc ggtacaacga gctggtcgag     300

cgcggtgagg ccgctctaga gcggctgcgc agccagcaga gcttcgagga agtgtcggcg     360

cgcgccgaag gctacgtgga ccaggcggtg gagttgaccc aggaggcgtt gggtacggtc     420

gcatcgcaga cccgcgcggt cggtgagcgt gccgccaagc tggtcggcat cgagctgcct     480

aagaaggctg ctccggccaa gaaggccgct ccggccaaga aggccgctcc ggccaagaag     540

gcggcggcca agaaggcgcc cgcgaagaag gcggcggcca agaa                      584
```

```
<210> SEQ ID NO 8
<211> LENGTH: 194
<212> TYPE: PRT
<213> ORGANISM: Mycobacterium bovis

<400> SEQUENCE: 8

Met Ala Glu Asn Ser Asn Ile Asp Asp Ile Lys Ala Pro Leu Leu Ala
1               5                   10                  15

Ala Leu Gly Ala Ala Asp Leu Ala Leu Ala Thr Val Asn Glu Leu Ile
            20                  25                  30
```

-continued

```
Thr Asn Leu Arg Glu Arg Ala Glu Glu Thr Arg Thr Asp Thr Arg Ser
        35                  40                  45

Arg Val Glu Glu Ser Arg Ala Arg Leu Thr Lys Leu Gln Glu Asp Leu
    50                  55                  60

Pro Glu Gln Leu Thr Glu Leu Arg Glu Lys Phe Thr Ala Glu Glu Leu
65                  70                  75                  80

Arg Lys Ala Ala Glu Gly Tyr Leu Glu Ala Ala Thr Ser Arg Tyr Asn
                85                  90                  95

Glu Leu Val Glu Arg Gly Glu Ala Ala Leu Glu Arg Leu Arg Ser Gln
            100                 105                 110

Gln Ser Phe Glu Glu Val Ser Ala Arg Ala Glu Gly Tyr Val Asp Gln
        115                 120                 125

Ala Val Glu Leu Thr Gln Glu Ala Leu Gly Thr Val Ala Ser Gln Thr
    130                 135                 140

Arg Ala Val Gly Glu Arg Ala Ala Lys Leu Val Gly Ile Glu Leu Pro
145                 150                 155                 160

Lys Lys Ala Ala Pro Ala Lys Lys Ala Ala Pro Ala Lys Lys Ala Ala
                165                 170                 175

Pro Ala Lys Lys Ala Ala Ala Lys Lys Ala Pro Ala Lys Lys Ala Ala
            180                 185                 190

Ala Lys


<210> SEQ ID NO 9
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 9

tttttgaatt ccatcatcat catcatcatc aaggagccgt tgct                       44


<210> SEQ ID NO 10
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 10

tttttgtcga cctattgagt caacctgggg gg                                   32


<210> SEQ ID NO 11
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 11

tttttgaatt ccatcatcat catcatcatg acacaactgt c                          41


<210> SEQ ID NO 12
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 12

tttttgtcga cctaagcgtc gatccc                                          26
```

<210> SEQ ID NO 13
<211> LENGTH: 41
<212> TYPE: DNA
<213> ORGANISM: Artificial Sequence
<220> FEATURE:
<223> OTHER INFORMATION: Synthetic oligonucleotide primer

<400> SEQUENCE: 13
tttttgaatt ccatcatcat catcatcatc ggacggtcta t 41

<210> SEQ ID NO 14
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 14
tttttgtcga ctcagtaagt ggaaatctcg tcct 34

<210> SEQ ID NO 15
<211> LENGTH: 44
<212> TYPE: DNA
<213> ORGANISM: Artificial Sequence
<220> FEATURE:
<223> OTHER INFORMATION: Synthetic oligonucleotide primer

<400> SEQUENCE: 15
tttttgaatt ccatcatcat catcatcatg ctgaaaactc gaac 44

<210> SEQ ID NO 16
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 16
tttttgtcga cctacttctg ggtgaccttc tt 32

<210> SEQ ID NO 17
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 17
tttttgtcga ccaaggagcc gttgct 26

<210> SEQ ID NO 18
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 18
tttttgaatt cctattgagt caacctgggg gg 32

<210> SEQ ID NO 19
<211> LENGTH: 26
<212> TYPE: DNA
<213> ORGANISM: Artificial Sequence
<220> FEATURE:

-continued

```
<223> OTHER INFORMATION: Synthetic oligonucleotide primer

<400> SEQUENCE: 19

tttttgtcga cgacacaact gtcgct                                    26


<210> SEQ ID NO 20
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 20

tttttgaatt cctaagcgtc gatccc                                    26


<210> SEQ ID NO 21
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 21

tttttgtcga ccggacggtc tat                                       23


<210> SEQ ID NO 22
<211> LENGTH: 34
<212> TYPE: DNA
<213> ORGANISM: Artificial Sequence
<220> FEATURE:
<223> OTHER INFORMATION: Synthetic oligonucleotide primer

<400> SEQUENCE: 22

ttttttgaat tccagtaagt ggaaatctcg tcct                           34


<210> SEQ ID NO 23
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 23

tttttgtcga cgctgaaaac tcgaac                                    26


<210> SEQ ID NO 24
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 24

tttttgaatt cctacttctg ggtgaccttc tt                             32
```

IMMUNOGENIC COMPOSITIONS COMPRISING *MYCOBACTERIUM BOVIS* SURFACE PROTEINS AND USES THEREOF

CROSS REFERENCE TO RELATED APPLICATIONS

This application is the U.S. National Stage of International Application No. PCT/US2019/014598, filed Jan. 22, 2019, which was published in English under PCT Article 21(2), which claims the benefit of U S. Provisional Application No. 62/620,047, filed Jan. 22, 2018, which is herein incorporated by reference in its entirety.

ACKNOWLEDGMENT OF GOVERNMENT SUPPORT

This invention was made with government support under 2017-67015-26638 awarded by National Institute of Food and Agriculture, USDA. The government has certain rights in the invention.

FIELD

This disclosure concerns immunogenic compositions that include *Mycobacterium bovis* surface antigens and their use for eliciting an immune response and/or immunizing against *M. bovis*.

BACKGROUND

Bovine tuberculosis (bTB) is a significant zoonotic threat that not only leads to significant animal losses associated with substantial economic consequences, but also creates a high risk for humans. The impact of bTB is estimated at US $3 billion per year globally (Waters et al., *Vaccine* 30:2611-2622, 2012). Due to the fact that bovine tuberculosis is very challenging to diagnose and impractical to treat, vaccination is still the most feasible approach to control infection. Currently, there is no vaccine available for bTB. Although some countries still utilize the human *Mycobacterium tuberculosis* vaccine (bacillus Calmette-Guérin—BCG) to immunize cattle, current bTB incidences indicate that it does not protect animals from infection. In addition, BCG immunization prior to or following challenge with bTB shows poor protection and does not improve outcome (Buddle et al., *Tuberculosis* (*Edinb*) 99:120-127, 2016).

*Mycobacterium bovis*, the primary causative agent of bTB, is an intracellular bacterium and because of this, cellular mediated immunity plays a pivotal role in controlling the infection (Lyashchenko et al., *Infect Immun* 72:2462-2467, 2004). Although there is sufficient evidence on the protective role of humoral immunity against *M. tuberculosis* infection (Achkar and Casadevall, *Cell Host Microbe* 13:250-262, 2013), antibody responses have been ignored as a component in the protection against bTB. Antibodies generated against specific mycobacterial surface antigens, in addition to significant cell-mediated immunity, activate essential protective responses against intracellular mycobacterial pathogens (Kohama et al., *Vaccine* 26:924-932, 2008).

Infection with *M. bovis* primarily affects the respiratory tract, although gastrointestinal disease in both humans and animals is not uncommon. In most cases, the pathogen can be transmitted from an infected animal to a naïve host by aerosol. Once inhaled, *M. bovis* readily establishes infection in the alveolar space of the lung (Fulton et al., *Am J Respir Cell Mol Biol* 22:333-343, 2000). Although macrophages are considered the primary host cells for *M. tuberculosis* infection, the chance that *M. bovis* will encounter the alveolar epithelial cells in the alveolus space is significantly greater than the chance the bacteria will encounter alveolar macrophages (Bermudez et al., *Infect Immun* 70:140-146, 2002). Alveolar epithelial cells are a critical first physiological barrier to prevent *M. bovis* entry into the bloodstream. Studies have demonstrated that lung mucosal cells play a significant role in the pathogenesis and immunity against tuberculosis infection (Nouailles et al., *J Clin Invest* 124:1268-1282, 2014; Harriff et al., *PLoS One* 9:e97515, 2014).

SUMMARY

The present disclosure describes surface proteins expressed by *M. bovis* under conditions that mimic the natural environment in a host, and use of the identified surface proteins in immunogenic compositions for immunization against *M. bovis*.

Provided herein are immunogenic compositions that include at least two, at least three or at least four *M. bovis* surface proteins. In some embodiments, the surface proteins are selected from Mb1524, MbO1_03198, phoY1_1 and hbhA, or proteins having at least 90% identity to Mb1524, MbO1_03198, phoY1_1 and hbhA. In some examples, the immunogenic compositions further include a pharmaceutically acceptable carrier and/or an adjuvant. The immunogenic compositions can be formulated for a particular route of administration, for example formulated for inhaled or intramuscular administration.

Also provided are methods of eliciting an immune response against *M. bovis* or an *M. bovis*antigen in a subject, or immunizing a subject against *M. bovis*, by administering an immunogenic composition disclosed herein. In some embodiments, the immunogenic composition is administered intranasally or intramuscularly.

Further provided herein are collections of plasmids that encode at least two, at least three or at least four *M. bovis* surface proteins. In some embodiments, the plasmids include a nucleotide sequence encoding Mb1524, MbO1_03198, phoY1_1 or hbhA, or a nucleotide sequence having at least 90% identity to the Mb1524, MbO1_03198, phoY1_1 or hbhA coding sequence.

The present disclosure also provides kits that include an immunogenic composition or a collection of plasmids disclosed herein.

The foregoing and other objects and features, of the disclosure will become more apparent from the following detailed description, which proceeds with reference to the accompanying figures.

BRIEF DESCRIPTION OF THE DRAWINGS

(FIG. 1A) Percentage of bacterial binding to A549 lung epithelial cells. (FIG. 1B) Percentage of bacterial binding to THP-1 macrophages. (FIG. 1C) Percentage of bacterial invasion of A549 cells. (FIG. 1D) Percentage of bacterial invasion of THP-1 cells. Results represent mean±standard error of three independent experiments. *, $P<0.05$, and **, $P<0.01$. Percentage of binding and invasion was calculated from the total *M. bovis* BCG inoculum added to cell monolayers at 0 minutes.

(FIG. 2A) Venn diagram showing the number of overlapping and unique bacterial surface proteins synthesized in granuloma-like and regular laboratory conditions. (FIG. 2B) Western blotting of *M. smegmatis* cell lysate overexpressing Mb1524, MbO1_03198, phoY1_1 and hbhA proteins using anti-His monoclonal antibody. Lane 1, pMV261-phoY1_1; Lane 2, pMV261-MbO1_03198; Lane 3, pMV261-hbhA; Lane 4, pMV261-Mb1524; Lane 5, pMV261 control. Arrows point to expressed target proteins.

(FIG. 5A) The colony forming units (CFUs) of *M. bovis*BCG were determined in the lungs of control non-immunized (PBS inhalation) mice and recombinant protein mix immunized mice (n=9/group) that were challenged with *M. bovis* BCG. Mice were sacrificed two weeks after the bacterial inoculation to identify viable BCG. The results are expressed as CFUs for the individual mice and the mean values for each group are provided. *P<0.05 (Student's t-test). **, P<0.01. (FIG. 5B) Histopathology of lungs of mice challenged with *M. bovis* BCG after inhalation of PBS (a) or recombinant protein immunization (b). Arrows point to bacteria in the lung tissue.

SEQUENCE LISTING

Figures 1A, 1B, 1C, 1D:
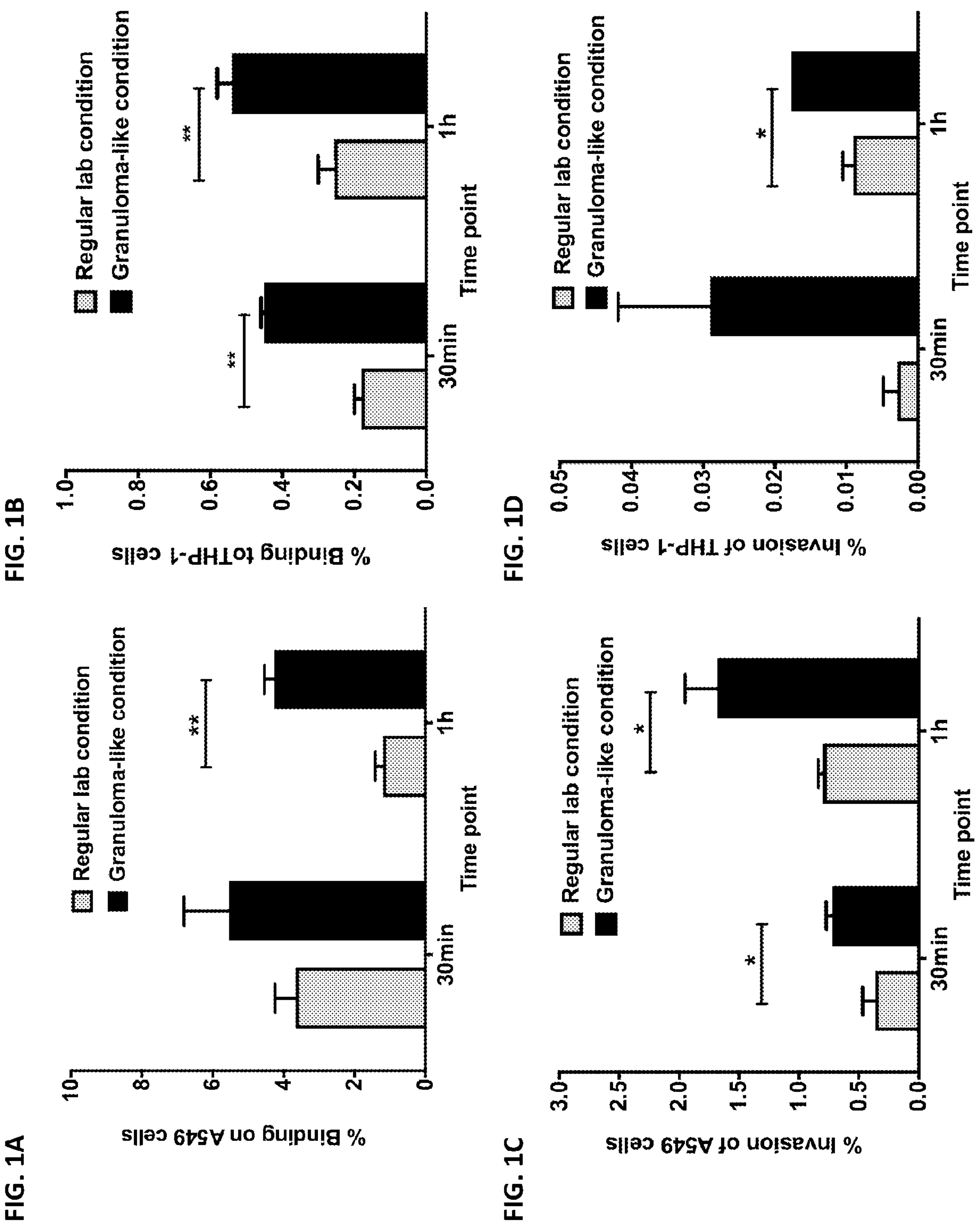
FIGS. 1A-1D: Binding and invasion assays of *M. bovis* BCG exposed to granuloma-like (pH 6.0, 0.3 M dextrose, anaerobic) and regular laboratory (pH 7.2, 20% $O_2$) conditions.

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file, created on Jul. 20, 2020, 15.8 KB, which is incorporated by reference herein. In the accompanying sequence listing:

SEQ ID NO: 1 is the nucleotide sequence encoding *M. bovis* antigen Mb1524.

SEQ ID NO: 2 is the amino acid sequence of *M. bovis* antigen Mb1524 (GenBank Accession No. P63694).

SEQ ID NO: 3 is the nucleotide sequence encoding *M. bovis* antigen MBO1_03198.

SEQ ID NO: 4 is the amino acid sequence of *M. bovis* antigen MBO1_03198 (GenBank Accession No. CEJ37080).

SEQ ID NO: 5 is the nucleotide sequence encoding *M. bovis* antigen phoY1_1.

SEQ ID NO: 6 is the amino acid sequence of *M. bovis* antigen phoY1_1 (GenBank Accession No. CCC65907).

SEQ ID NO: 7 is the nucleotide sequence encoding *M. bovis* antigen hbhA.

SEQ ID NO: 8 is the amino acid sequence of *M. bovis* antigen hbhA (GenBank Accession No. WP 024456635).

SEQ ID NOs: 9-24 are oligonucleotide primer sequences.

DETAILED DESCRIPTION

I. Abbreviations

BCG bacillus Calmette-Guérin
bTB bovine tuberculosis
CFU colony forming units
ELISA enzyme-linked immunosorbent assay
IP intraperitoneal
MDBK Madin-Darby bovine kidney
MOI multiplicity of infection II. Terms and Methods Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the disclosure, the following explanations of specific terms are provided:

Adjuvant: A substance or vehicle that non-specifically enhances the immune response to an antigen (for example, a *M. bovis* antigen). Adjuvants can be used with the compositions disclosed herein, for example as part of a *M. bovis* vaccine composition provided herein. Adjuvants can include a suspension of minerals (alum, aluminum hydroxide, or aluminum phosphate) on which antigen is adsorbed; or water-in-oil emulsion in which antigen solution is emulsified in mineral oil (for example, Freund's incomplete adjuvant), sometimes with the inclusion of killed mycobacteria (Freund's complete adjuvant) to further enhance antigenicity. Another adjuvant is monophosphoryl lipid A (MPL), which is an immune-stimulating lipid. MPL can be combined with alum to produce the AS04 adjuvant, which is used in some approved vaccines, such as the human papillomavirus vaccine Cervarix. Another combination adjuvant is AS03, which combines α-tocopherol, squalene and polysorbate 80 in an oil-in-water emulsion. Immunostimulatory oligonucleotides (such as those including a CpG motif) can also be used as adjuvants (for example, see U.S. Pat. Nos. 6,194,388; 6,207,646; 6,214,806; 6,218,371;

6,239,116; 6,339,068; 6,406,705; and 6,429,199), as well as poly(I:C), which is a synthetic double-stranded RNA that mimics a molecular pattern associated with viral infection. Adjuvants also include biological molecules, such as costimulatory molecules. Exemplary biological adjuvants include IL-2, RANTES, GM-CSF, TNF-α, IFN-γ, G-CSF, LFA-3, CD72, B7-1, B7-2, OX-40L and 41 BBL. In one example the adjuvant is one or more a toll-like receptor (TLR) agonists, such as an agonist of TLR1/2 (which can be a synthetic ligand) (for example, Pam3Cys), TLR2 (for example, CFA, Pam2Cys), TLR3 (for example, polyl:C, poly A:U), TLR4 (for example MPLA, Lipid A, and LPS), TLR5 (for example flagellin), TLR7 (for example gardiquimod, imiquimod, loxoribine, Resiquimod®), TLR7/8 (for example, R0848), TLR8 (for example, imidazoquionolines, ssPolyU, 3M-012), TLR9 (for example, ODN 1826 (type B), ODN 2216 (type A), CpG oligonucleotides) and/or TLR11/12 (for example, profilin). In one example, the adjuvant is TiterMax® Gold Adjuvant (Sigma-Aldrich), which is a water-in-oil adjuvant containing a block copolymer (CRL-8300), squalene and sorbitan monooleate.

Administer: As used herein, administering a composition (such as one containing one or more *M. bovis* antigens) to a subject means to give, apply or bring the composition into contact with the subject. Administration can be accomplished by any of a number of routes, such as, for example, intramuscular, intranasal, pulmonary, topical, oral, subcutaneous, intraperitoneal, intravenous, intrathecal and intradermal.

Antigen or immunogen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens.

Cell-mediated immunity: An immune response that does not involve antibodies, but rather involves the activation of phagocytes, natural killer (NK) cells, antigen-specific cytotoxic T-lymphocytes, and the release of various cytokines in response to an antigen. Historically, the immune system was separated into two branches—humoral immunity, for which the protective function of immunization could be found in the humor (cell-free bodily fluid or serum) and cellular immunity, for which the protective function of immunization was associated with cells. $CD4^+$ T cells or helper T cells provide protection against different pathogens. Cytotoxic T cells cause death by apoptosis without using cytokines, therefore in cell mediated immunity cytokines are not always present. Cellular immunity protects the body by activating antigen-specific cytotoxic T-lymphocytes that are able to induce apoptosis in body cells displaying epitopes of foreign antigen on their surface, such as virus-infected cells, cells with intracellular bacteria, and cancer cells displaying tumor antigens; activating macrophages and natural killer cells, enabling them to destroy pathogens; and stimulating cells to secrete a variety of cytokines that influence the function of other cells involved in adaptive immune responses and innate immune responses. Cell-mediated immunity is directed primarily at microbes that survive in phagocytes and microbes that infect non-phagocytic cells.

HbhA (heparin-binding hemagglutinin): A surface protein expressed by *M. bovis*. HbhA is a virulence factor that mediates bacterial binding to epithelial cells and other non-phagocytic cells. HbhA also plays a role in extrapulmonary dissemination during tuberculosis infection. The hbhA protein sequence is deposited under GenBank Accession No. WP_024456635. Nucleotide and amino acid sequences of hbhA are set forth herein as SEQ ID NOs: 7 and 8, respectively.

Heterologous: Originating from separate genetic sources or species. For example, a peptide that is heterologous to an *M. bovis* protein originates from a species other than *M. bovis*. In some embodiments, the heterologous protein or peptide includes a protein tag, such as a His tag.

Immune response: A response of a cell of the immune system, such as a B-cell, T-cell, macrophage or polymorphonucleocyte, to a stimulus such as an antigen or vaccine (such as a *M. bovis* antigen or vaccine). An immune response can include any cell of the body involved in a host defense response, including for example, an epithelial cell that secretes an interferon or a cytokine. An immune response includes, but is not limited to, an innate immune response or inflammation. As used herein, a protective immune response refers to an immune response that protects a subject from infection (prevents infection or prevents the development of disease associated with infection). Methods of measuring immune responses are well known in the art and include, for example, measuring proliferation and/or activity of lymphocytes (such as B or T cells), secretion of cytokines or chemokines, inflammation, antibody production and the like.

Immunize: To render a subject (such as a mammal) protected from an infectious disease (for example, bTB), such as by vaccination.

Immunogenic composition: A term used herein to mean a composition useful for stimulating or eliciting a specific immune response (or immunogenic response) in a subject. The immunogenic composition includes two or more *M. bovis* surface antigens. In some embodiments, the immunogenic response is protective or provides protective immunity, in that it enables the subject to better resist infection with or disease progression from the pathogen against which the immunogenic composition is directed. In some embodiments, an "effective amount" or "immune-stimulatory amount" of an immunogenic composition is an amount which, when administered to a subject, is sufficient to engender a detectable immune response. Such a response may comprise, for instance, generation of an antibody specific to one or more of the epitopes provided in the immunogenic composition. Alternatively, the response may comprise a T-helper or CTL-based response to one or more of the epitopes provided in the immunogenic composition. All three of these responses may originate from naïve or memory cells.

Isolated: An "isolated" biological component (such as a nucleic acid or protein) has been substantially separated or purified away from other biological components (such as cell debris, or other proteins or nucleic acids). Biological components that have been "isolated" include those components purified by standard purification methods. The term also embraces recombinant nucleic acids and proteins, as well as chemically synthesized nucleic acids or peptides.

MBO1_03198: A surface protein expressed by *M. bovis*. MBO1_03198 is a protein that contains the diacylglycerol kinase family enzyme motif involved in lipid transport and metabolism, and domains of transcriptional regulator XRE-family helix-turn-helix and transcription elongation factor GreA/GreB, C-term. It is disclosed herein that overexpression of MbO1_03198 leads to increased binding to and invasion of mucosal cells. The MbO1_03198 protein sequence is deposited under GenBank Accession No. CEJ37080. Nucleotide and amino acid sequences of MbO1_03198 are set forth herein as SEQ ID NOs: 3 and 4, respectively.

Mb1524: A surface protein expressed by *M. bovis*. Mb1524 is a protein containing the conserved domain of the regulator of protease activity HflC, stomatin/prohibitin superfamily, whose function is unknown. It is disclosed herein that overexpression of Mb1524 leads to increased binding to and invasion of mucosal cells. The Mb1524 protein sequence is deposited under GenBank Accession No. P63694. Nucleotide and amino acid sequences of Mb1524 are set forth herein as SEQ ID NOs: 1 and 2, respectively.

*Mycobacterium bovis*: An intracellular bacterium that is the causative agent of bovine tuberculosis (bTB). *M .bovis* is related to *M. tuberculosis*, which causes TB in humans.

Bovine TB is a chronic infectious disease that can infect a broad range of mammalian hosts, including humans, cattle, bison, deer, llamas, pigs, goats, domestic cats, foxes, coyotes, possum and rodents. Infection with *M. bovis* can be spread by exhaled air (for example in aerosol droplets) or by contact with sputum, urine, feces or pus of an infected animal.

Pharmaceutically acceptable vehicles: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa, $21^{st}$ Edition (2005) describes compositions and formulations suitable for pharmaceutical delivery of one or more immunogenic compositions, such as one or more *M. bovis* immunogenic compositions disclosed herein, and additional pharmaceutical agents.

PhoY1_1 (phosphate-transport system transcriptional regulatory protein phoU homolog 1 phoY1): A surface protein expressed by *M. bovis*. It is disclosed herein that overexpression of phoY1_1 on the surface of *M. bovis* helps the bacteria to better bind and invade epithelial cells. The phoY1_1 protein sequence is deposited under GenBank Accession No. CCC65907. Nucleotide and amino acid sequences of phoY1_1 are set forth herein as SEQ ID NOs: 5 and 6, respectively.

Preventing, treating or ameliorating a disease: "Preventing" a disease refers to inhibiting the full development of a disease. "Treating" refers to a therapeutic intervention that ameliorates a sign or symptom of a disease or pathological condition after it has begun to develop. "Ameliorating" refers to the reduction in the number or severity of signs or symptoms of a disease.

Purified: The term "purified" does not require absolute purity; rather, it is intended as a relative term. Thus, for example, a purified protein, nucleic acid or other compound is one that is isolated in whole or in part from naturally associated proteins and other contaminants. In certain embodiments, the term "substantially purified" refers to a protein, nucleic acid or other active compound that has been isolated from a cell, cell culture medium, or other crude preparation and subjected to fractionation to remove various components of the initial preparation, such as proteins, cellular debris, and other components.

Subject: Living multi-cellular vertebrate organisms, a category that includes both human and non-human mammals, such as non-human primates. In some examples, the subject is an animal that can be infected with *Mycobacterium bovis*, such as a bovine (including, for example, cattle, bison, buffalo and ox) or another susceptible animal, such as a human, non-human primate, elk, deer, goat, cat, dog, pig, badger or possum.

Therapeutically effective amount: A quantity of a specified agent sufficient to achieve a desired effect in a subject being treated with that agent. For example, this may be the amount of an immunogenic composition useful for eliciting an immune response in a subject and/or for preventing infection or disease caused by *M. bovis*. In one example, a therapeutically effective amount of an immunogenic composition is an amount sufficient to increase resistance to, prevent, ameliorate, and/or treat infection caused by *M. bovis* in a subject without causing a substantial cytotoxic effect in the subject. The effective amount of an immunogenic composition useful for increasing resistance to, preventing, ameliorating, and/or treating infection in a subject will be dependent on, for example, the subject being treated, the manner of administration of the therapeutic composition and other factors.

Vaccine: A preparation of immunogenic material capable of stimulating an immune response, administered for the prevention, amelioration, or treatment of disease, such as an infectious disease. The immunogenic material may include an immunogenic composition disclosed herein. Vaccines may elicit both prophylactic (preventative) and therapeutic responses. Methods of administration vary according to the vaccine, but can include inoculation, ingestion, intranasal, intramuscular or other forms of administration. Vaccines may be administered with an adjuvant to enhance the immune response.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. "Comprising A or B" means including A, or B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present disclosure, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

Disclosed herein is the identification of several surface proteins that are expressed by *M. bovis* during infection of a host. These surface antigens are also expressed on the form of *M. bovis* that is transmitted from an infected host to a new host. Four of the identified *M. bovis* antigens, Mb1524, Mb01_03198, phoY1_1 and hbhA, were further characterized and found to promote binding to and invasion of mucosal cells. Thus, the disclosed *M. bovis* surface proteins can be used, for example, in immunogenic compositions for immunization against *M. bovis*.

The present disclosure describes immunogenic compositions that include at least one, at least two, at least three or at least four *M. bovis* surface proteins. At least one, at least two, at least three or at least four of the surface proteins are selected from Mb1524 (e.g., SEQ ID NO: 2), MbO1_03198 (e.g., SEQ ID NO: 4), phoY1_1 (e.g., SEQ ID NO: 6), and hbhA (e.g., SEQ ID NO: 8), or proteins having at least 80%, at least 85%, at least 90%, at least 95%, at least 96%, at least 97%, at least 98% or at least 99% identity to Mb1524, MbO1_03198, phoY1_1 and hbhA.

Provided herein are immunogenic compositions that include at least one, at least two, at least three or at least four surface proteins from *M. bovis*. In some embodiments, the at least one, at least two, at least three or at least four surface proteins are selected from a protein comprising at least 80%, at least 85%, at least 90%, at least 95%, at least 96%, at least 97%, at least 98% or at least 99% sequence identity with the amino acid sequence of SEQ ID NO: 2; a protein comprising at least 80%, at least 85%, at least 90%, at least 95%, at least 96%, at least 97%, at least 98% or at least 99% sequence identity with the amino acid sequence of SEQ ID NO: 4; a protein comprising at least 80%, at least 85%, at least 90%, at least 95%, at least 96%, at least 97%, at least 98% or at least 99% sequence identity with the amino acid sequence of SEQ ID NO: 6; and a protein comprising at least 80%, at least 85%, at least 90%, at least 95%, at least 96%, at least 97%, at least 98% or at least 99% sequence identity with the amino acid sequence of SEQ ID NO: 8.

In some embodiments, the immunogenic composition includes two surface proteins from *M. bovis*. In particular examples, the immunogenic composition includes a protein comprising the amino acid sequence of SEQ ID NO: 2 and a protein comprising the amino acid sequence of SEQ ID NO: 4. In other particular examples, the immunogenic composition includes a protein comprising the amino acid sequence of SEQ ID NO: 2 and a protein comprising the amino acid sequence of SEQ ID NO: 6. In other particular examples, the immunogenic composition includes a protein comprising the amino acid sequence of SEQ ID NO: 2 and a protein comprising the amino acid sequence of SEQ ID NO: 8. In other particular examples, the immunogenic composition includes a protein comprising the amino acid sequence of SEQ ID NO: 4 and a protein comprising the amino acid sequence of SEQ ID NO: 6. In other particular examples, the immunogenic composition includes a protein comprising the amino acid sequence of SEQ ID NO: 4 and a protein comprising the amino acid sequence of SEQ ID NO: 8. In other particular examples, the immunogenic composition includes a protein comprising the amino acid sequence of SEQ ID NO: 6 and a protein comprising the amino acid sequence of SEQ ID NO: 8.

In some embodiments, the immunogenic composition includes three surface proteins from *M. bovis*. In particular examples, the immunogenic composition includes a protein comprising the amino acid sequence of SEQ ID NO: 2, a protein comprising the amino acid sequence of SEQ ID NO: 4 and a protein comprising the amino acid sequence of SEQ ID NO: 6. In other particular examples, the immunogenic composition includes a protein comprising the amino acid sequence of SEQ ID NO: 2, a protein comprising the amino acid sequence of SEQ ID NO: 4 and a protein comprising the amino acid sequence of SEQ ID NO: 8. In other particular examples, the immunogenic composition includes a protein comprising the amino acid sequence of SEQ ID NO: 2, a protein comprising the amino acid sequence of SEQ ID NO: 6 and a protein comprising the amino acid sequence of SEQ ID NO: 8. In other particular examples, the immunogenic composition includes a protein comprising the amino acid sequence of SEQ ID NO: 4, a protein comprising the amino acid sequence of SEQ ID NO: 6 and a protein comprising the amino acid sequence of SEQ ID NO: 8.

In some embodiments, the immunogenic composition includes four surface proteins from *M. bovis*. In particular examples, the immunogenic composition includes a protein comprising the amino acid sequence of SEQ ID NO: 2, a protein comprising the amino acid sequence of SEQ ID NO: 4, a protein comprising the amino acid sequence of SEQ ID NO: 6 and a protein comprising the amino acid sequence of SEQ ID NO: 8.

In some embodiments, one or more of the surface proteins includes a heterologous peptide, such as a protein tag. The protein tag can include, for example, an affinity tag, an epitope tag, a fluorescent protein, an enzyme or a carrier protein. In particular examples, the protein tag is a histidine tag, chitin binding protein, maltose binding protein, glutathione-S-transferase, V5, c-myc, HA, FLAG, GFP or another well-known fluorescent protein.

In some embodiments, the immunogenic composition further includes a pharmaceutically acceptable carrier.

In some embodiments, the immunogenic composition further includes an adjuvant. In some examples, the adjuvant includes unmethylated CpG oligodeoxynucleotides (CpG ODNs). In some examples, the adjuvant comprises an oil-in-water adjuvant, such as an oil-in-water emulsion. In some examples, the water-in-oil adjuvant comprises squalene, a block copolymer (such as CRL-8300) and/or sorbitan monooleate. In specific examples, the adjuvant includes TiterMax® Gold Adjuvant (Sigma-Aldrich). In other examples, the adjuvant includes alum, such as aluminum phosphate or aluminum hydroxide. In specific non-limiting examples, the adjuvant is AS03 or AS04.

In some embodiments, the immunogenic composition is formulated for intranasal administration. In other embodiments, the immunogenic composition is formulated for intramuscular administration.

Also provided are methods of eliciting an immune response against *M. bovis* or an *M. bovis* antigen in a subject. In some embodiments, the method includes administering to the subject an immunogenic composition disclosed herein. Further provided are methods of immunizing a subject against *M. bovis* by administering to the subject an immunogenic composition disclosed herein. In some embodiments, the immunogenic composition is administered intranasally. In other embodiments, the immunogenic composition is administered intramuscularly. In some embodiments, the subject is a non-human animal. In some examples, the subject is a bovine subject, such as a cow.

The present disclosure also provides kits that include an immunogenic composition disclosed herein. In some embodiments, the kit further includes instructions for administration of the immunogenic composition and/or a description of the components of the immunogenic composition.

Further provided by the present disclosure are single plasmids or collections of plasmids that encode at least one, at least two, at least three or at least four *M. bovis* surface proteins. In some embodiments, the plasmids include a nucleotide sequence encoding Mb1524 (e.g., SEQ ID NO: 1), MbO1_03198 (e.g., SEQ ID NO: 3), phoY1_1 (e.g., SEQ ID NO: 5), or hbhA (e.g., SEQ ID NO: 7), or a nucleotide sequence having at least 80%, at least 85%, at least 90%, at least 95%, at least 96%, at least 97%, at least 98% or at least 99% identity to the Mb1524, MbO1_03198, phoY1_1 or hbhA coding sequence.

Provided herein is a plasmid that encodes a *M. bovis* surface antigen. In some embodiments, the surface antigen is encoded by a nucleotide sequence at least 80%, at least 85%, at least 90%, at least 95%, at least 96%, at least 97%, at least 98% or at least 99% identical to SEQ ID NO: 1, SEQ ID NO: 3, SEQ ID NO: 5 or SEQ ID NO: 7. In some examples, the plasmid further includes a heterologous sequence, such as a heterologous promoter or a sequence encoding a heterologous protein, for example a protein tag.

Also provided are collections of plasmids that include at least one, at least two, at least three or at least four plasmids encoding surface proteins from *M. bovis*. In some embodiments, the collection of plasmids includes at least two plasmids selected from a plasmid comprising a nucleotide sequence at least 80%, at least 85%, at least 90%, at least 95%, at least 96%, at least 97%, at least 98% or at least 99% identical to SEQ ID NO: 1, a plasmid comprising a nucleotide sequence at least 80%, at least 85%, at least 90%, at least 95%, at least 96%, at least 97%, at least 98% or at least 99% identical to SEQ ID NO: 3, a plasmid comprising a nucleotide sequence at least 80%, at least 85%, at least 90%, at least 95%, at least 96%, at least 97%, at least 98% or at least 99% identical to SEQ ID NO: 5 and a plasmid comprising a nucleotide sequence at least 80%, at least 85%, at least 90%, at least 95%, at least 96%, at least 97%, at least 98% or at least 99% identical to SEQ ID NO: 7.

In some embodiments, the collection of plasmids includes two plasmids that each encode a different *M. bovis* surface antigen. In some examples, the collection includes a plasmid comprising the nucleotide sequence of SEQ ID NO: 1 and a plasmid comprising the nucleotide sequence of SEQ ID NO: 3. In other examples, the collection includes a plasmid comprising the nucleotide sequence of SEQ ID NO: 1 and a plasmid comprising the nucleotide sequence of SEQ ID NO: 5. In other examples, the collection includes a plasmid comprising the nucleotide sequence of SEQ ID NO: 1 and a plasmid comprising the nucleotide sequence of SEQ ID NO: 7. In other examples, the collection includes a plasmid comprising the nucleotide sequence of SEQ ID NO: 3 and a plasmid comprising the nucleotide sequence of SEQ ID NO: 5. In other examples, the collection includes a plasmid comprising the nucleotide sequence of SEQ ID NO: 3 and a plasmid comprising the nucleotide sequence of SEQ ID NO: 7. In other examples, the collection includes a plasmid comprising the nucleotide sequence of SEQ ID NO: 5 and a plasmid comprising the nucleotide sequence of SEQ ID NO: 7.

In some embodiments, the collection of plasmids includes three plasmids that each encode a different *M. bovis* surface antigen. In some examples, the collection includes a plasmid comprising the nucleotide sequence of SEQ ID NO: 1, a plasmid comprising the nucleotide sequence of SEQ ID NO: 3 and a plasmid comprising the nucleotide sequence of SEQ ID NO: 5. In other examples, the collection includes a plasmid comprising the nucleotide sequence of SEQ ID NO: 1, a plasmid comprising the nucleotide sequence of SEQ ID NO: 3 and a plasmid comprising the nucleotide sequence of SEQ ID NO: 7. In other examples, the collection includes a plasmid comprising the nucleotide sequence of SEQ ID NO: 1, a plasmid comprising the nucleotide sequence of SEQ ID NO: 5 and a plasmid comprising the nucleotide sequence of SEQ ID NO: 7. In other examples, the collection includes a plasmid comprising the nucleotide sequence of SEQ ID NO: 3, a plasmid comprising the nucleotide sequence of SEQ ID NO: 5 and a plasmid comprising the nucleotide sequence of SEQ ID NO: 7.

In some embodiments, the collection includes four plasmids that each encode a different *M. bovis* surface antigen. In some examples, the collection includes a plasmid comprising the nucleotide sequence of SEQ ID NO: 1, a plasmid comprising the nucleotide sequence of SEQ ID NO: 3, a plasmid comprising the nucleotide sequence of SEQ ID NO: 5 and a plasmid comprising the nucleotide sequence of SEQ ID NO: 7.

In some examples, at least one, at least two, at least three or at least four of the plasmids of the collection further include a heterologous sequence, such as a heterologous promoter or a sequence encoding a heterologous protein, for example a protein tag.

Further provided herein are kits that include a plasmid or a collection of plasmids disclosed herein. In some embodiments, each plasmid is in a separate container. In some examples, the kit further includes transfection reagents, cell culture media, instructions for protein expression and/or a description of the components of the plasmid or plasmids.

IV. BCG Antigens and Polynucleotides

Bovine tuberculosis (bTB) is a highly transmissible infection and remains of great concern as a zoonosis. The worldwide incidence of bTB is rising, creating a potential reservoir and increased infection risk for humans and animals. Thus, a need exists for an effective vaccine against bTB.

Mucosal vaccination with BCG using the natural route of infection has been a challenge (Manjaly Thomas et al., *Trans R Soc Trop Med Hyg* 109:175-181, 2015). Despite this, it has been shown that vaccination with BCG leads to the generation of weak effector memory T cells and tissue resident memory cells. The response lacks mucosal chemokine receptors (Beverley et al., *Mucosal Immunol* 7:20-26, 2014). Studies of the mucosal vaccine against *M. tuberculosis* in humans indicates feasibility of the vaccine to prevent infection (Caetano et al., *J Biomed Nanotechnol* 10:2295-2316, 2014; Diogo and Reljic, *Immunotherapy* 6:1001-1013, 2014). Although there is a high degree of similarity between *M. bovis* and *M. tuberculosis* (Gamier et al., *Proc Natl Acad Sci USA* 100:7877-7882, 2003), mucosal vaccination of animals against *M. bovis* infection has not been previously reported.

To identify novel surface antigens of *M. bovis* as inducers of protective immunity, surface proteomics of the *M. bovis* BCG strain cultured under granuloma-like conditions (to mimic the natural environment) was investigated. The present disclosure demonstrates that bacteria exposed to a biologically relevant environment have greater ability to bind and invade host cells than bacteria incubated under regular laboratory conditions. A total of 957 surface-exposed proteins were identified on BCG cultured under standard laboratory conditions, whereas 1097 proteins were expressed by bacteria under the granuloma-like condition. The overexpression of four of these surface proteins, Mb1524, MbO1_03198, PhoY1 and HbhA, on *M. smegmatis* led to increased binding and invasion of mucosal cells. Immunogenicity of purified recombinant proteins as well as *M. smegmatis* overexpressing these surface antigens was evaluated in mice. Significant levels of specific IgA and IgG antibodies were observed in the recombinant protein immunized groups by both inhalation and intraperitoneal (IP) routes but only IP delivery induced high total IgA and IgG levels. Significant differences in antibody levels in the *M. smegmatis* group that overexpressed surface antigens were not detected. A significant reduction of bacterial load in lungs was observed only in mice immunized with the inhaled recombinant proteins. This data indicates that administration of BCG recombinant protein via inhalation leads to activation of mucosal immunity and confers protection against *M. bovis* BCG infection.

The nucleotide and amino acid sequences of the four characterized *M. bovis* surface antigens are provided below and set forth herein as SEQ ID NOs: 1-8.

```
Mb1524 nucleotide sequence
                                          (SEQ ID NO: 1)
GTGCAAGGAGCCGTTGCTGGTCTGGTGTTTCTGGCCGTCCTGGTGA

TTTTCGCCATCATCGTGGTGGCCAAGTCGGTGGCGCTGATCCCGCA

GGCGGAGGCCGCGGTGATCGAGCGGCTGGGTCGCTATAGTCGTACG

GTCAGTGGGCAGTTGACGCTGTTGGTGCCGTTCATCGACCGCGTCC

GGGCTCGGGTGGACCTGCGCGAGCGGGTGGTGTCGTTTCCGCCGCA

ACCGGTGATCACCGAGGACAACTTGACGCTGAACATCGACACCGTC

GTCTACTTCCAGGTGACCGTTCCGCAGGCGGCGGTGTACGAGATCA

GCAATTACATCGTCGGGGTCGAACAGCTCACCACCACCACCACCCT
```

-continued

GCGCAACGTTGTCGGCGGGATGACGCTGGAGCAGACGTTGACCTCG

CGTGACCAGATCAACGCCCAGCTGCGCGGCGTTCTCGATGAGGCGA

CCGGCCGCTGGGGTCTGCGGGTGGCGCGGGTGGAGCTGCGCAGCAT

CGATCCGCCGCCGTCGATTCAGGCGTCGATGGAAAAGCAGATGAAG

GCCGACCGGGAGAAGCGAGCGATGATTCTGACCGCCGAAGGTACCC

GGGAGGCGGCGATAAAACAGGCCGAGGGGCAAAAGCAGGCGCAGAT

CCTGGCCGCCGAGGGCGCCAAGCAGGCCGCGATCTTGGCTGCTGAG

GCCGATCGGCAGTCTCGGATGCTGCGCGCTCAGGGTGAGCGCGCCG

CGGCCTACCTGCAGGCGCAAGGGCAGGCCAAGGCCATCGAGAAGAC

GTTCGCCGCGATCAAGGCTGGCCGGCCCACCCCGGAGATGCTGGCC

TACCAATACCTGCAGACGCTGCCGGAGATGGCGCGTGGGGACGCCA

ACAAGGTATGGGTGGTGCCCAGCGACTTCAACGCCGCACTGCAGGG

TTCACCAGGCTGCTGGGCAAGCCGGGTGAGGACGGGGTGTTCCGGT

TCGAGCCGTCCCCGGTCGAAGACCAGCCCAAGCACGCGGCCGACGG

TGACGACGCCGAGGTCGCCGGCTGGTTCTCCACCGATACCGACCCG

TCGATCGCTCGGGCGGTGGCTACAGCCGAGGCGATAG

Mb1524 amino acid sequence
(SEQ ID NO: 2)

MQGAVAGLVFLAVLVIFAIIVVAKSVALIPQAEAAVIERLGRYSRT

VSGQLTLLVPFIDRVRARVDLRERVVSEPPQPVITEDNLTLNIDTV

VYEQVTVPQAAVYEISNYIVGVEQLTTTTLRNVVGGMTLEQTLTSR

DQINAQLRGVLDEATGRWGLRVARVELRSIDPPPSIQASMEKQMKA

DREKRAMILTAEGTREAAIKQAEGQKQAQILAAEGAKQAAILAAEA

DRQSRMLRAQGERAAAYLQAQGQAKAIEKTFAAIKAGRPTPEMLAY

QYLQTLPEMARGDANKVWVVPSDFNAALQGFTRLLGKPGEDGVFRF

EPSPVEDQPKHAADGDDAEVAGWFSTDTDPSIARAVATAEAIARKP

VEGSLGTPPRLTQ

MBO1_03198 nucleotide sequence
(SEQ ID NO: 3)

GTGGACACAACTGTCGCTACCATGATCAGCAAATACATACAGATAA

CCGTTTGCTCTTGGAGCCCGGTGGAGGTCACATCGATGAGCACGAC

GTTCGCTGCCCGCCTGAACCGCCTGTTCGACACGGTTTATCCGCCC

GGACGCGGGCCACATACCTCCGCGGAGGTGATCGCGGCGCTCAAGG

CAGAGGGCATCACGATGTCGGCTCCCTACCTATCACAGCTACGCTC

AGGAAACCGTACGAACCCATCGGGGGCGACCATGGCCGCCCTGGCC

AACTTCTTCCGCATCAAGGCGGCCTACTTCACCGACGACGAGTACT

ACGAAAAGCTCGACAAGGAATTGCAGTGGCTGTGCACGATGCGCGA

CGACGGCGTGCGCCGGATCGCGCAGCGGGCCCACGGGTTGCCCTCC

GCGGCGCAGCAGAAGGTGTTGGACCGGATCGACGAGCTGCGGCGTG

CCGAAGGGATCGACGCTTAG

MBO1_03198 amino acid sequence
(SEQ ID NO: 4)

MDTTVATMISKYIQITVCSWSPVEVTSMSTTFAARLNRLFDTVYPP

GRGPHTSAEVIAALKAEGITMSAPYLSQLRSGNRTNPSGATMAALA

NFFRIKAAYFTDDEYYEKLDKELQWLCTMRDDGVRRIAQRAHGLPS

AAQQKVLDRIDELRRAEGIDA phoY1_1nucleotide sequence
(SEQ ID NO: 5)

ATGCGGACGGTCTATCACCAGCGGCTAACCGAGTTGGCCGGACGAT

TGGGAGAGATGTGCAGCCTGGCCGGGATAGCGATGAAACGCGCAAC

GCAGGCTCTGCTCGAGGCCGACATTGGCGCCGCTGAACAAGTAATC

CGTGACCATGAGCGGATCGTGGCGATGCGAGCCCAAGTCGAAAAGG

AAGCGTTCGCGCTGCTGGCGTTGCAACATCCGGTGTCCGGCGAGCT

GCGGGAAATCTTCAGTGCGGTGCAGATCATCGCCGACACCGAGCGC

ATGGGTGCGTTGGCTGTGCATATTGCCAAGATCACCCGACGCGAGT

ATCCGAACCAGGTGCTTCCTGAGGAAGTTCGCAACTGCTTCGCCGA

CATGGCGAAGGTGGCAATCGCGTTGGGTGACAGTGCAAGACAAGTG

CTGGTGAACCGTGACCCGCAGGAAGCCGCGCAACTGCACGATCGTG

ACGACGCGATGGATGACCTGCATAGGCATTTGCTGAGCGTGCTGAT

AGATCGAGAATGGCGGCACGGCGTTCGCGTCGGTGTGGAAACGGCG

TTGCTGGGTCGTTTCTTTGAGCGCTTCGCCGACCACGCTGTGGAAG

TGGGCCGCCGCGTCATCTTCATGGTCACCGGGGTGCTACCGACCGA

GGACGAGATTTCCACTTACTGA phoY1_1 amino acid sequence
(SEQ ID NO: 6)

MRTVYHQRLTELAGRLGEMCSLAGIAMKRATQALLEADIGAAEQVI

RDHERIVAMRAQVEKEAFALLALQHPVSGELREIFSAVQIIADTER

MGALAVHIAKITRREYPNQVLPEEVRNCFADMAKVAIALGDSARQV

LVNRDPQEAAQLHDRDDAMDDLHRHLLSVLIDREWRHGVRVGVETA

LLGRFFERFADHAVEVGRRVIFMVTGVLPTEDEISTY hbhA nucleotide sequence
(SEQ ID NO: 7)

ATGGCTGAAAACTCGAACATTGATGACATCAAGGCTCCGTTGCTTG

CCGCGCTTGGAGCGGCCGACCTGGCCTTGGCCACTGTCAACGAGTT

GATCACGAACCTGCGTGAGCGTGCGGAGGAGACTCGTACGGACACC

CGCAGCCGGGTCGAGGAGAGCCGTGCTCGCCTGACCAAGCTGCAGG

AAGATCTGCCCGAGCAGCTCACCGAGCTGCGTGAGAAGTTCACCGC

CGAGGAGCTGCGTAAGGCCGCCGAGGGCTACCTCGAGGCCGCGACT

AGCCGGTACAACGAGCTGGTCGAGCGCGGTGAGGCCGCTCTAGAGC

GGCTGCGCAGCCAGCAGAGCTTCGAGGAAGTGTCGGCGCGCGCCGA

AGGCTACGTGGACCAGGCGGTGGAGTTGACCCAGGAGGCGTTGGGT

ACGGTCGCATCGCAGACCCGCGCGGTCGGTGAGCGTGCCGCCAAGC

TGGTCGGCATCGAGCTGCCTAAGAAGGCTGCTCCGGCCAAGAAGGC

-continued

CGCTCCGGCCAAGAAGGCCGCTCCGGCCAAGAAGGCGGCGGCCAAG

AAGGCGCCCGCGAAGAAGGCGGCGGCCAAGAA hbhA amino acid sequence (SEQ ID NO: 8)

MAENSNIDDIKAPLLAALGAADLALATVNELITNLRERAEETRTDT

RSRVEESRARLTKLQEDLPEQLTELREKFTAEELRKAAEGYLEAAT

SRYNELVERGEAALERLRSQQSFEEVSARAEGYVDQAVELTQEALG

TVASQTRAVGERAAKLVGIELPKKAAPAKKAAPAKKAAPAKKAAAK

KAPAKKAAAK

V. Administration of Immunogenic Compositions

The disclosed compositions can be administered to a subject by any of the routes normally used for introducing immunogenic compositions (such as vaccines) into a subject. Methods of administration include, but are not limited to, intradermal, intramuscular, intraperitoneal, parenteral, intravenous, subcutaneous, mucosal, vaginal, rectal, intranasal, inhalation or oral. Parenteral administration, such as subcutaneous, intravenous or intramuscular administration, is generally achieved by injection. Injectables can be prepared in conventional forms, either as liquid solutions or suspensions, solid forms suitable for solution or suspension in liquid prior to injection, or as emulsions. Injection solutions and suspensions can be prepared from sterile powders, granules, tablets, and the like. Administration can be systemic or local.

The immunogenic compositions disclosed herein can be administered with at least one pharmaceutically acceptable carrier. Pharmaceutically acceptable carriers are determined in part by the particular composition being administered, as well as by the particular method used to administer the composition. Accordingly, there is a wide variety of suitable formulations of pharmaceutical compositions of the present disclosure. Pharmaceutically acceptable carriers include, but are not limited to, saline, buffered saline, dextrose, water, glycerol, sesame oil, ethanol, and combinations thereof. The composition can also contain conventional pharmaceutical adjunct materials such as, pharmaceutically acceptable salts to adjust the osmotic pressure, buffers, preservatives and the like. The carrier and composition can be sterile, and the formulation suits the mode of administration. The composition can also contain minor amounts of wetting or emulsifying agents, or pH buffering agents. The composition can be a liquid solution, suspension, emulsion, tablet, pill, capsule, sustained release formulation, or powder.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like.

Some of the compositions may potentially be administered as a pharmaceutically acceptable acid- or base-addition salt, formed by reaction with inorganic acids such as hydrochloric acid, hydrobromic acid, perchloric acid, nitric acid, thiocyanic acid, sulfuric acid, and phosphoric acid, and organic acids such as formic acid, acetic acid, propionic acid, glycolic acid, lactic acid, pyruvic acid, oxalic acid, malonic acid, succinic acid, maleic acid, and fumaric acid, or by reaction with an inorganic base such as sodium hydroxide, ammonium hydroxide, potassium hydroxide, and organic bases such as mono-, di-, trialkyl and aryl amines and substituted ethanolamines.

In some embodiments, the immunogenic compositions provided herein are formulated for mucosal vaccination, such as oral, intranasal, pulmonary, rectal or vaginal administration. In a specific example, this is achieved by intranasal administration. For example, the disclosed compositions can include one or more biodegradable, mucoadhesive polymeric carriers. Polymers such as polylactide-co-glycolide (PLGA), chitosan (for example in the form of chitosan nanoparticles, such as N-trimethyl chitosan (TMC)-based nanoparticles), alginate (such as sodium alginate) and carbopol can be included. In one example the composition includes one or more hydrophilic polymers, such as sodium alginate or carbopol. In one example, the composition includes carbopol, for example in combination with starch. In one example, the composition is formulated as a particulate delivery system used for nasal administration. Thus, the composition can include liposomes, immune-stimulating complexes (ISCOMs) and/or polymeric particles. The compositions can also include one or more lipopeptides of bacterial origin, or their synthetic derivatives, such as Pam3Cys, (Pam2Cys, single/multiple-chain palmitic acids and lipoamino acids (LAAs). The compositions can also include one or more adjuvants, such as one or more of CpG oligodeoxynucleotides (CpG ODN), Flt3 ligand, and monophosphoryl lipid A (MLA). In one example, the adjuvant includes TiterMax® Gold Adjuvant (Sigma-Aldrich).

The disclosed compositions can be administered as a single dose or as multiple doses (for example, boosters). In some examples, the first administration is followed by a second administration. For example, the second administration can be with the same, or with a different *M. bovis* immunogenic composition than the first composition administered (for example, greater or fewer *M. bovis* antigens, or a different group of *M. bovis* antigens). In a specific example, the second administration is with the same immunogenic composition as the first composition administered. In another specific example, the second administration is with a different composition than the first composition administered.

In some examples, the immunogenic compositions are administered as multiple doses, such as 2, 3, 4, 5, 6, 7, 8, 9 or 10 doses (such as 2-3 doses). In such examples, the timing between the doses can be at least 1 week, at least 2 weeks, at least 3 weeks, at least 4 weeks, at least 6 weeks, at least 8 weeks, at least 12 weeks, at least 2 months, at least 3 months, at least 4 months, at least 5 months, at least 6 months, at least 1 year, at least 2 years or at least 5 years, such as 1-4 weeks, 2-3 weeks, 1-6 months, 2-4 months, 1 week, 2 weeks, 3 weeks, 4 weeks, 5 weeks, 6 weeks, 7 weeks, 8 weeks, 9 weeks, 10 weeks, 12 weeks, 1 month, 2 months, 3, months, 4, months, 5 months, 6 months, 1 year, 2 years, 5 years or 10 years, or combinations thereof (such as where there are at least three administrations, wherein the timing between the first and second, and second and third doses, can be the same or different).

The dose administered to a subject in the context of the present disclosure should be sufficient to induce a beneficial therapeutic response in a subject over time, or to inhibit or prevent *M. bovis* infection and/or the development of bTB. The dose required can vary from subject to subject depending on the species, age, weight and general condition of the subject, the severity of the infection being treated, the particular composition being used and its mode of administration. An appropriate dose can be determined by one of ordinary skill in the art using only routine experimentation.

The following examples are provided to illustrate certain particular features and/or embodiments. These examples should not be construed to limit the disclosure to the particular features or embodiments described.

EXAMPLES

Example 1

Materials and Methods

This example describes the materials and experimental procedures used for the studies described in Example 2.

Bacteria

*Mycobacterium bovis* BCG Pasteur and *Mycobacterium smegmatis* mc$^2$ 155 strains were cultured on Middlebrook 7H10 agar supplemented with 10% oleic acid, albumin, dextrose, and catalase to log phase (Hardy Diagnostics, Santa Maria, Calif.). Prior to the assays, the BCG Pasteur strain was resuspended in 2 ml of Hanks' balanced salt solution (HBSS) and passed through a 23-gauge needle 10 times. After a 10-minute rest, the top 1 ml was adjusted to McFarland standard 2 (approximately $3\times10^8$ cells/ml) and used as the inoculum. The inoculum was observed under the microscope to ensure dispersal of the sample. In addition, serial dilutions were plated for CFU reads to calculate exact concentration of the inoculum. Viability of BCG was determined by the LIVE-DEAD® assay (Molecular Probes, Eugene, Oreg.).

Cell Culture

A549 human type II alveolar epithelial cells, MDBK cells and THP-1 cells were purchased from ATCC. A549 cells and MDBK cells were maintained in DMEM supplemented with 10% heat-inactivated fetal bovine serum. A total of $10^5$ cells were added to each well of a 24-well tissue culture plate. Human mononuclear phagocyte THP-1 cells were cultured in RPMI-1640 medium supplemented with 10% heat-inactivated fetal bovine serum. THP-1 cells were treated with 20 ng/ml phorbol 12-myristate 13-acetate (PMA, Sigma) and seeded in tissue culture plates for 24 hours to allow for maturation. The next day, monolayers were replenished with fresh RPMI-1640 medium and rested for an additional 48 hours. Cells were seeded at 90% confluence.

Environmental Conditions

BCG were incubated in two different conditions: (1) regular laboratory culture condition: 37° C., 20% $O_2$ and pH 7.2; and (2) granuloma-like condition: increased osmolarity in 7H9 broth supplemented with 0.3 M dextrose and no oxygen. An oxygen deficient condition was obtained in an anaerobic jar (VWR) with pH 6.0 at 37° C. After 24 hours of incubation, bacteria were washed at 4° C., re-suspended in HBSS, passed through a 23-gauge needle 10 times and used for further assays.

Invasion and Binding Assay

A549 cells and MDBK cells were infected with live BCG at a multiplicity of infection (MOI) of 10 bacteria per host cell for 30 minutes or 1 hour and either incubated at 4° C. for the binding or 37° C. for the invasion assay. The cell monolayers were gently washed three times with PBS and then permeabilized with 0.1% Triton X-100 for 15 minutes. Cell lysates were plated onto 7H10 agar plates and bacterial CFUs were quantified after three weeks of incubation.

Biotin Labeling and Purification of BCG Surface Proteins

*M. bovis* BCG culture from different conditions were resuspended in 1 mg of Sulfo-NHS-LC-biotin (Pierce, Rockford, Ill.) reconstituted in 1 ml HBSS. Bacteria were biotin labeled for 30 minutes at 4° C. with gentle agitation. The unbound Sulfo-NHS-LC-biotin was inactivated and removed by washing bacteria three times with 10 mM glycine in HBSS. Labeled bacteria were resuspended in the guanidinium lysis buffer (10 mM EDTA, 2 mM EGTA, 0.1% Tween-20, 6 mM guanidinuim-HCl, in PBS, pH 7.2) and disrupted by bead-milling machine using 100-μm glass beads (Sigma, St. Louis, Mo.). Samples were cleared by centrifugation at 15,000 rpm for 5 minutes. The supernatants were processed for isolation of biotinylated proteins out of the total protein sample by affinity purification with magnetic streptavidin-coated C1 Dynabeads (Invitrogen). Briefly, aliquots of 1.5 ml protein sample was incubated for 1 hour at 23° C. with 80 μl of C1 Dynabeads and microcentrifuged. The beads were washed twice with the guanidinium lysis buffer followed by washing with 0.05% Tween-20 in PBS (pH 7.2). Beads were resuspended in 35 μl of 1% SDS supplemented with 10 mM EDTA in $H_2O$ and incubated at 65° C. for 10 minutes. Forty-five μl of 2× Laemmli buffer was added to each sample, boiled for 10 minutes and then cleared by centrifugation 2,000 rpm for 10 minutes. Biotinylated proteins were visualized by SDS-PAGE.

Overexpression of *M. bovis* BCG Proteins in *M. Smegmatis*

*M. bovis* BCG selected genes were amplified using Fideli-Taq PCR Master Mix (Affymetrix, Santa Clara, Calif.) using the primers listed in the Table 1. The 6xHis tag was incorporated into the primers. PCR-generated fragments were cloned into the mycobacterial shuttle vector pMV261 containing HSP60 promoter and kanamycin resistant marker. The resulting plasmids were propagated in *Escherichia coli* DH10B and then electroporated into *M. smegmatis* mc$^2$ 155. Transformants were selected on 50 μg/ml of kanamycin containing Middlebrook 7H10 agar plates and screened by PCR for the kanamycin gene. Protein expression in *M. smegmatis* was confirmed by Western Blotting using the anti-HIS probe antibody.

TABLE 1

Primers used for construction of *M. smegmatis* clones overexpressing *M. bovis* BCG surface antigens in the pMV261 vector

| Genes | Primers | SEQ ID NO: |
|---|---|---|
| Mb1524 | 5'-TTTTTGAATTCCATCATCATCATCATCATCAAGGAGCCGTTGCT-3' | 9 |
| | 5'-TTTTTGTCGACCTATTGAGTCAACCTGGGGGG-3' | 10 |
| MbO1_03198 | 5'-TTTTTGAATTCCATCATCATCATCATCATGACACAACTGTC-3' | 11 |
| | 5'-TTTTTGTCGACCTAAGCGTCGATCCC-3' | 12 |
| phoY1_1 | 5'-TTTTTGAATTCCATCATCATCATCATCATCGGACGGTCTAT-3' | 13 |
| | 5'-TTTTTGTCGACTCAGTAAGTGGAAATCTCGTCCT-3' | 14 |

TABLE 1-continued

Primers used for construction of *M. smegmatis* clones overexpressing *M. bovis* BCG surface antigens in the pMV261 vector

| Genes | Primers | SEQ ID NO: |
|---|---|---|
| HBHA | 5'-TTTTTGAATTCCATCATCATCATCATC ATGCTGAAAACTCGAAC-3' | 15 |
| | 5'-TTTTTGTCGACCTACTTCTGGGTGACC TTCTT-3' | 16 |

Expression and Purification of *M. Bovis* BCG Recombinant Proteins

*M. bovis* BCG selected genes were amplified using Fideli-Taq PCR Master Mix (Affymetrix, Santa Clara, Calif.) using the primers listed in the Table 2. The PCR-generated fragments were cloned into a pET6xHN-N vector encoding ampicillin resistance. The resulting plasmids were transformed into B121 (DE3) cells and transformant colonies were selected on LB agar plates containing 100 μg/ml of ampicillin. Protein expression in *E. coli* was confirmed by Western Blotting using the anti-HIS probe antibody. Briefly, samples of 150 mg of bacteria were harvested and resuspended in 700 μl 0.5%SDS with 0.5% protease inhibitor cocktail (Sigma). Bacteria were mechanically disrupted in a bead-milling machine with 0.1 mm silica beads (6 cycles, 20 seconds each at max speed). Lysates were centrifuged at 12,000 g for 5 minutes and supernatants were mixed with Laemmli buffer (+5% BME). The remaining pellets were also processed and resuspended in 200 μl denaturing buffer (500 mM NaCl, 7 M urea, 20 mM Tris-HCl, 10 mM imidazole) and Laemmli buffer (+5% BME). Both soluble and non-soluble samples were boiled for 10 minutes, run on 12% Mini-PROTEAN precast SDS-PAGE gel (Biorad, Hercules, Calif.) and transferred to a nitrocellulose membrane. After a 1-hour exposure with the blocking buffer (4% BSA with PBS-Tween) at room temperature, the membranes were further incubated with anti-HIS monoclonal antibody for 1 hour followed by incubation with IRDye-680 streptavidin (Licor, Lincoln, Nebr.) according to the manufacturer's protocol. Biotinylation patterns were visualized on an Odyssey Scanner (Licor).

TABLE 2

Primers used for construction of recombinant *M. bovis* BCG surface antigens in the pET6xHN_N vector of *E. coli*

| Genes | Primers | SEQ ID NO: |
|---|---|---|
| Mb1524 | 5'-TTTTTGTCGACCAAGGAGCCGTTGCT-3' | 17 |
| | 5'-TTTTTGAATTCCTATTGAGTCAACCTGGG GGG-3' | 18 |
| MbO1_03198 | 5'-TTTTTGTCGACGACACAACTGTCGCT-3' | 19 |
| | 5'-TTTTTGAATTCCTAAGCGTCGATCCC-3' | 20 |
| phoY1_1 | 5'-TTTTTGTCGACCGGACGGTCTAT-3' | 21 |
| | 5'-TTTTTTGAATTCCAGTAAGTGGAAATCT CGTCCT-3' | 22 |
| HBHA | 5'-TTTTTGTCGACGCTGAAAACTCGAAC-3' | 23 |
| | 5'-TTTTTGAATTCCTACTTCTGGGTGACCTT CTT-3' | 24 |

Vaccination and Challenge of Mice

TiterMax® Gold Adjuvant was purchased from Sigma-Aldrich. A total of 6 groups (9 mice in each group) of six-week-old female C57BL/6 mice were used in this study. Equal amounts of purified recombinant proteins were mixed together at a total concentration of 50 μg. At this concentration, 100 μl was used for intraperitoneal injections and 20 μl for inhalation. *M. smegmatis* clones overexpressing the target *M. bovis* BCG proteins were mixed together and a total amount of $10^7$ CFUs were used for inhalation. Boost was carried out 1.5 weeks after primary immunization.

The groups with 9 mice in each group were set as follows:

1) Intraperitoneal immunization using 50 μg purified mixed recombinant proteins with the TiterMax® Gold Adjuvant;
2) Intraperitoneal injection with PBS in the TiterMax® Gold Adjuvant as a control for adjuvant effects;
3) Inhalation with 50 μg purified mixed recombinant proteins;
4) Inhalation with PBS;
5) Inhalation with $10^7$ *M. smegmatis* overexpressing the target *M. bovis* BCG proteins;
6) Inhalation with $10^7$*M. smegmatis* with pMV261 vector as a control.

Three weeks post-vaccination, all mice were intranasally challenged with $10^7$ BCG Pasteur strain pre-exposed to the granuloma-like conditions. Two weeks later, antisera were collected for IgG detection and lungs for IgA detection. One mouse in each group was euthanized for histological section, others were euthanized to determine the bacterial load. The organs were homogenized, debris removed by filtration, and serially diluted samples were plated on the Middlebrook 7H10 agar plates for the CFU counts of bacilli. The number of viable bacteria was counted after three weeks of incubation at 37° C.

IgG Detection

Total levels of IgG were detected using a commercially available kit (eBioscience, Vienna, Austria) according to the manufacturer's protocol. Briefly, 96-well plates were coated with 100 μL/well of capture antibody (pre-titrated, purified anti-mouse IgG monoclonal antibody) in PBS buffer overnight at 4° C. The wells were washed two times with PBS and blocked overnight at 4° C. Wells were incubated with 10 μL/well diluted (1:100) sera and 50 μL/well diluted detection antibody (pre-titrated, HRP-conjugated anti-mouse IgG polyclonal antibody) for 2 hours followed by three washes with PBS. The substrate solution (tetramethylbenzidine) was added for 15 minutes, and the reaction was stopped with stop solution of 2N $H_2SO_4$. Plates were recorded at 450 nm wavelength. The standard curve was made to quantify the total IgG levels. Five μg/ml mixed *M. bovis* BCG recombinant proteins were used to coat the 96-well plate to detect the specific IgG followed by the same steps as described for total IgG. No standard was used for the specific IgG.

IgA Detection

Total levels of IgA were detected using a commercial kit (eBioscience, Vienna, Austria) according to the manufacturer's protocol. Briefly, 96-well plates were coated with 100 μL/well of capture antibody (pre-titrated, purified anti-mouse IgA monoclonal antibody) in PBS buffer overnight at 4° C. The wells were washed two times with PBS and blocked overnight at 4° C. Wells were incubated with 10 μL/well diluted (1:50) lung homogenates and 50 μL/well diluted detection antibody (pre-titrated, HRP-conjugated anti-mouse IgA polyclonal antibody) for 3 hours at room temperature followed by four washes with PBS. Substrate solution was added for 15 minutes, and the reaction was stopped with 2N $H_2SO_4$. Plates were recorded at 450 nm wavelength. The standard curve was created to quantify the total IgA levels.

Five μg/ml mixed *M. bovis* BCG recombinant proteins were used to coat the 96-well plate to detect specific IgA followed by the same steps as described for total IgA. Lung homogenates were 20 times diluted for specific IgA detection. No standard was used for specific IgA.

Statistical Analysis

In vitro experiments were repeated at least three times and data shown are means of the replicates and standard error. The student's t-test was used, and variance between experimental groups was assessed by one-way ANOVA. A value of $p < 0.05$ was considered to be significant. Graph Pad Prism software version 5.0 was used for statistical analysis.

Example 2

*Mycobacterium Bovis* BCG Surface Antigens Expressed under Granuloma-Like Conditions as Inducers of Protective Immunity This example describes studies to determine whether exposure to granuloma-like conditions influences the ability of *M. bovis* to bind and invade host cells, if granuloma-like conditions effect the composition of *M. bovis* surface proteins, if overexpression of surface antigens promotes the binding and invasion ability of *M. bovis*, and if bacterial surface antigens induce mucosal immunity in vivo.

The Granuloma-Like Environment Enhances *M. Bovis* BCG Binding and Invasion of Lung Epithelial A549 and THP-1 Macrophage-Like Cells

*M. bovis* BCG Pasteur strain was exposed to either standard laboratory conditions (pH 7.2, aerobic, 37° C.) or granuloma-like conditions (pH 6.0, anaerobic, 0.3 M dextrose, 37° C.) for 24 hours. Cell binding and invasion capability of *M. bovis* BCG exposed to each condition was tested. Bacteria were exposed to A549 epithelial cells and THP-1 macrophages for 30 minutes and 1 hour at 4° C. *M. bovis* BCG exposed to the environment mimicking the granuloma-like condition was able to bind to A549 cells with significantly greater efficiency than bacteria cultured in regular laboratory conditions (FIG. 1A). Similarly, *M. bovis* BCG exposed to the granuloma-like condition bound with significantly greater efficiency to THP-1 macrophages compared to bacteria cultured in regular laboratory conditions at both time points (FIG. 1B).

Invasion assays were carried out to determine whether different environmental conditions could influence *M. bovis* uptake by lung epithelial cells and macrophages. Bacteria were exposed to A549 epithelial cells and THP-1 macrophages for 30 minutes and 1 hour at 37° C. *M. bovis* BCG exposed to the granuloma-like condition was able to invade A549 epithelial cells and THP-1 macrophages with significantly greater efficiency than bacteria cultured in regular laboratory conditions at 1 hour post infection. Differences in *M. bovis* BCG uptake were also observed at 30 minutes post infection in both cell lines.

Figure 2A:
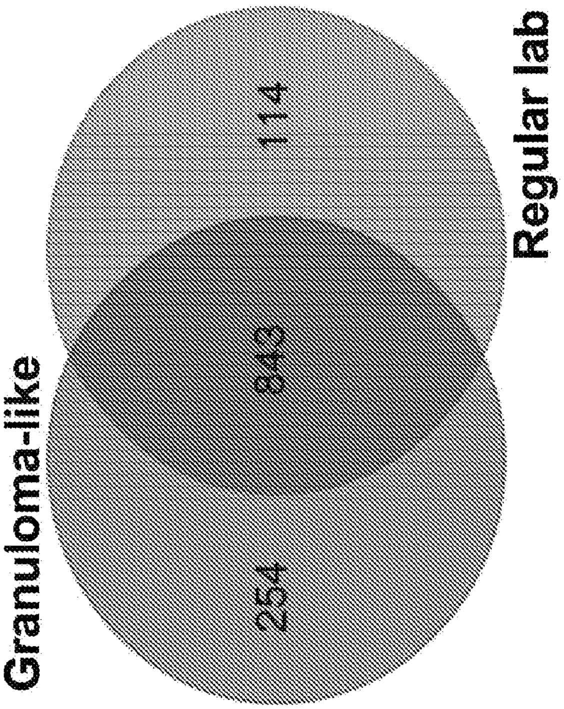
FIGS. 2A-2B: *M. bovis* BCG surface proteins expressed in different conditions.

Proteomic Analysis of the Surface of *M. Bovis* BCG Exposed to Biologically Relevant Conditions Since *M. bovis* BCG exposure to the granuloma-like condition induced efficient binding to and invasion of host cells, studies were carried out to identify surface molecules that contribute to these phenotypes. *M. bovis* BCG surface proteins were profiled to identify changes between the regular laboratory and granuloma-like conditions. To do this, *M. bovis* BCG surface exposed proteins were selectively labeled and extracted for mass spectrometry analysis. A total of 1211 proteins were detected by mass spectrometry in both samples. Analysis of *M. bovis* BCG cultured in regular laboratory conditions identified 957 proteins, whereas 1097 proteins were identified for *M. bovis* BCG cultured in the granuloma-like condition. A Venn diagram (FIG. 2A) shows that 114 of the proteins detected in the regular lab condition cultured *M. bovis* BCG were absent in *M. bovis* BCG cultured in the granuloma-like condition; while 254 proteins were uniquely expressed in *M. bovis* BCG cultured in the granuloma-like condition. Twelve proteins were selected for further studies.

*M. Smegmatis* Clones Overexpressing *M. Bovis* BCG Surface Proteins Efficiently Bind and Invade Host Cells

Figure 2B:
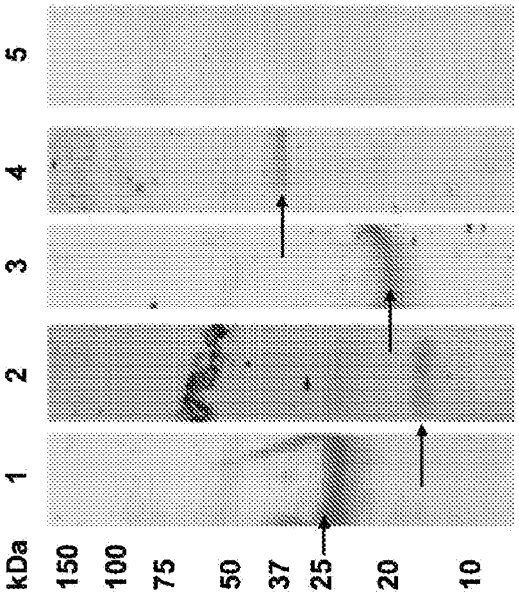

*M. smegmatis* is a fast growing non-pathogenic mycobacteria that poorly binds and invades host epithelial cells, but is efficiently taken up by macrophages. In order to determine if the selected *M. bovis* BCG proteins contribute to host cell binding and invasion, *M. smegmatis* clones expressing all twelve *M. bovis* BCG surface exposed proteins were constructed. Using western blotting, it was found that *M. bovis* Mb1524, MbO1_03198, phoY1_1 and hbhA proteins were successfully expressed in *M. smegmatis* $mc^2$ 155 (FIG. 2B).

Figure 3A:
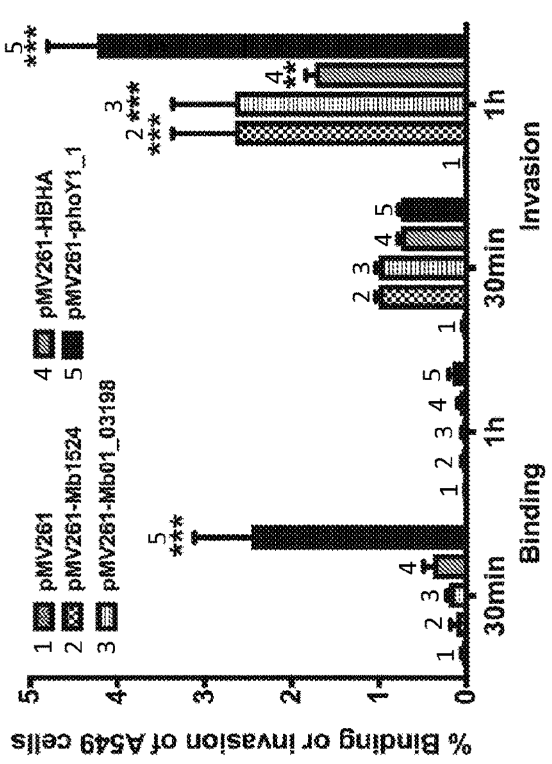
FIGS. 3A-3B: Binding and invasion assays of A549 cells (FIG. 3A) and Madin-Darby bovine kidney (MDBK) cells (FIG. 3B) using *M. smegmatis* overexpressing pMV261-Mb1524, pMV261-MbO1_03198, pMV261-phoY1_1 and pMV261-hbhA constructs. Results represent mean ±standard error of three independent experiments. *, P<0.05, , P<0.01, *, P<0.0001 compared with the control pMV261construct of *M. smegmatis.*
Figure 3B:
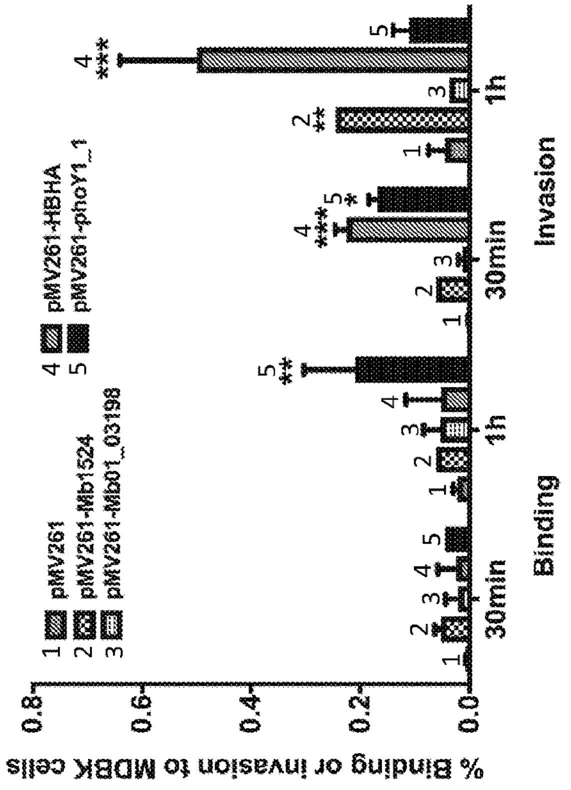

The overexpressed clones, along with an *M. smegmatis* control containing just the pMV261 vector, were tested for their ability to bind and invade A549 and bovine MDBK epithelial cells. While *M. smegmatis* overexpression of the phoY1_1 protein had significantly higher binding ability compared to the three other clones at 30 minutes post-infection (FIG. 3A), all four clones were able to invade A549 cells with greater efficiency than control *M. smegmatis* containing the pMV261 vector at both time points. Only the *M. smegmatis* phoY1_1 clone showed significantly greater binding ability to MDBK cells at 1 hour compared with the control. The invasion experiments of MDBK cells demonstrated that the clones expressing the hbhA and phoY1_1 proteins had a significantly higher percentage of invasion than the other clones at 30 minutes post-infection. *M. smegmatis* overexpressing the Mb1524 protein invaded better than control bacteria only at 1 hour (FIG. 3B).

Figures 4A, 4B, 4C, 4D:
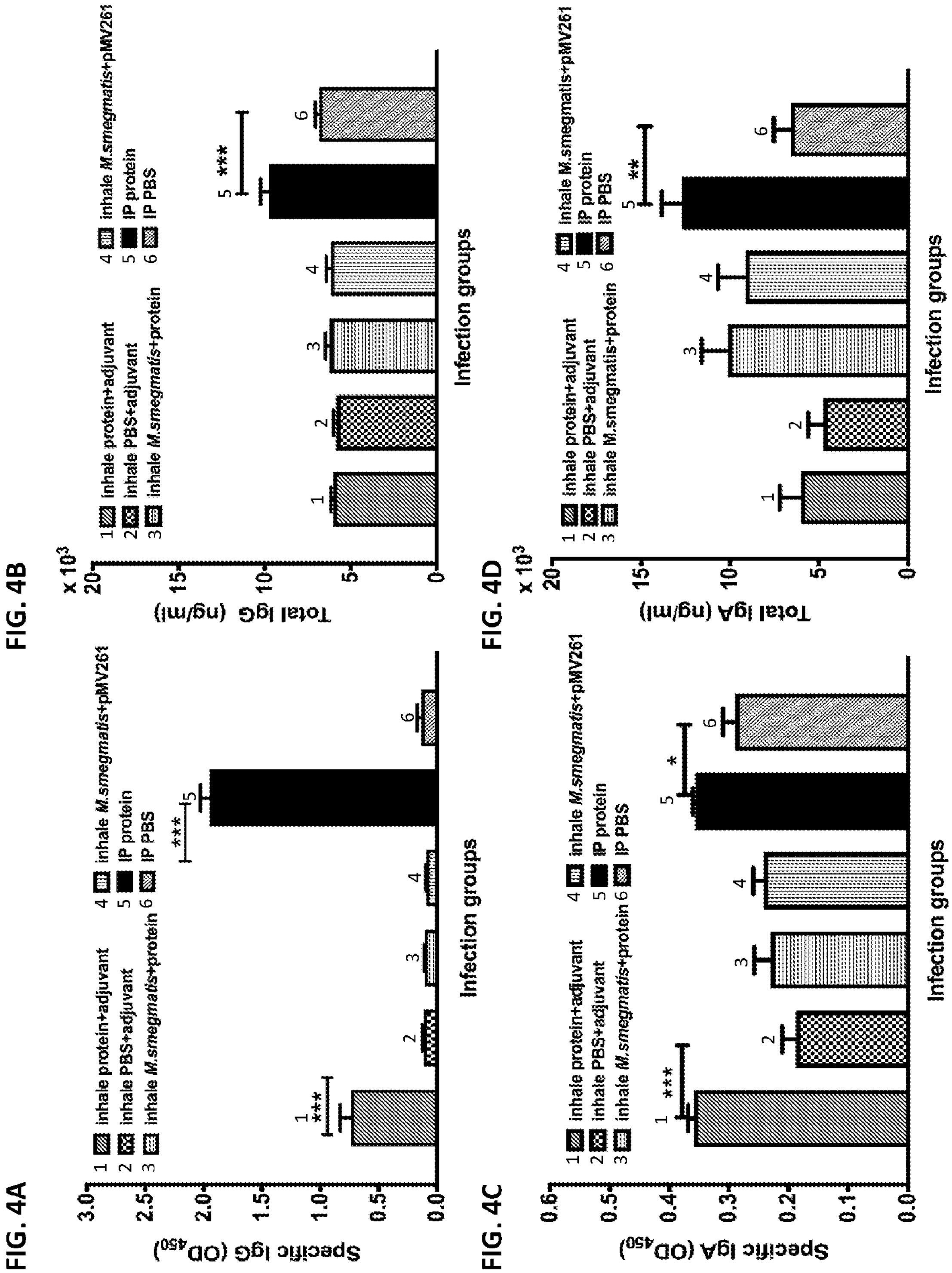
FIGS. 4A-4D: Specific and total antibody responses in C57BL/6 mice (n=9/group) immunized either intranasally or intraperitoneally with a mixture of four recombinant *M. bovis* surface antigens or with *M. smegmatis* clones overexpressing the four antigens. All experimental groups of mice were intranasally challenged with $10^7$ BCG pre-exposed to the granuloma-like conditions and two weeks later, antisera were collected for IgG and lungs were collected for IgA detection by ELISA. The results for specific IgG (FIG. 4A) and IgA (FIG. 4C) are presented as $OD_{450}$, whereas total IgG (FIG. 4B) and IgA (FIG. 4D) levels were calculated in ng/ml for the individual mice, and the mean values for each group are provided. *, P<0.05,  P<0.01, *, P<0.0001.

*M. Bovis* Recombinant Proteins Induce Protective Immunity in Mice Immunized by Inhalation and IP Routes A first group of mice were immunized intranasally with a mixture of *M. bovis* Mb1524, MbO1_03198, phoY1_1 and hbhA recombinant proteins and TiterMax® Gold adjuvant. Phosphate buffered saline with adjuvant was used to immunize a control group of mice. A second group of mice was administered a mix of *M. smegmatis* clones overexpressing *M. bovis* surface proteins by intraperitoneal injection. An *M. smegmatis* clone with empty pMV261 vector served as a control. Studies were then performed to determine whether these immunization strategies could trigger protective immunity. Serum was collected from all mice and IgG levels were determined. It was found that mice immunized with recombinant protein by either inhalation or intraperitoneal routes had significantly higher levels of specific IgG antibody synthesized in the blood compared with the control groups (FIG. 4A). A significantly greater level of total IgG was identified in mice immunized with recombinant protein by IP injection (FIG. 4B), but no significant changes were observed in other experimental groups when compared to the control group.

To analyze mucosal antibody responses in the airway, IgA levels were measured. The results showed that production of IgA exhibited a similar trend as IgG. The recombinant protein immunized group showed significantly higher levels of specific IgA antibody when immunized via either inhalation or IP, but no significant changes were observed in other experimental groups when compared with the control groups (FIG. 4C). The significant production of total IgA antibody was observed only in the experimental group of mice immunized with recombinant proteins via the IP route (FIG. 4D).

Bacterial Loads in the Lungs of Pre-Immunized and BCG Challenge Groups

Figure 5A:
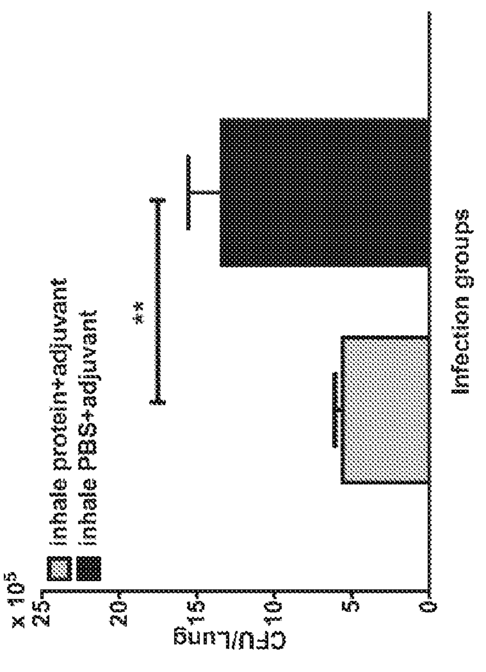
FIGS. 5A-5B: The number of viable bacteria in the lungs of BCG challenged mice.
Figure 5B:
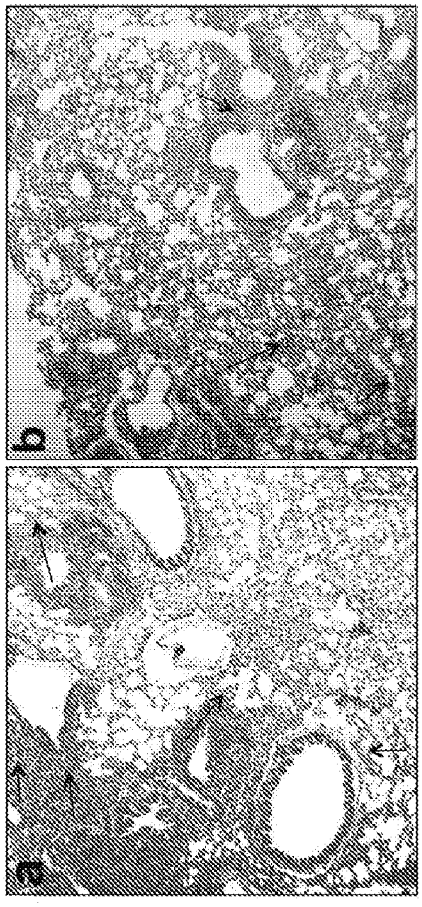

To measure the protective efficacy of immunization, bacterial load was determined in the lungs of the experimental and control groups of mice during the intranasal BCG challenge. The results demonstrate that bacterial CFUs were significantly reduced in the lungs of mice immunized via inhalation with the mix of recombinant proteins compared with the inhaled PBS plus adjuvant control group (FIG. 5).

Summary

*M. bovis* present within an active tuberculosis cavity is immersed in an environment that is completely different from normal laboratory conditions, and thus the phenotype of bacteria in the biologically relevant environment differs from *M. bovis* grown in culture. The studies disclosed herein identified proteomic changes on the bacterial surface during exposure to the granuloma-like condition, and characterized some of the proteins that have a role in bacterial pathogenesis and/or contribute to host immune responses. These data demonstrate that *M. bovis* BCG cultured in the granuloma-like condition binds and invades A549 epithelial cells, THP-1 macrophages and MDBK epithelial cells more efficiently than bacteria exposed to the regular laboratory condition.

A comparative proteomics approach was used to identify bacterial surface proteins unique to the granuloma-like condition, and then selected surface proteins were tested for their ability to increase bacterial binding and invasion. Proteins Mb1524, MbO1_03198 and phoY1_1 were differentially expressed in *M. bovis* BCG cultured in granuloma-like condition. The hbhA protein was also selected for further studies because it contributes to bacterial interaction with epithelial cells and plays role in extrapulmonary dissemination during tuberculosis infection (Pethe et al., *Nature* 412:190-194, 2001; Silva et al., *Infect Immun* 81:2645-2659, 2013).

The selected *M. bovis* surface proteins expressed in the granuloma-like condition were found to play a role in binding and invasion of host cells, and induced a mucosal immune response in mice. The Mb1524 gene encodes a protein containing the conserved domain of the regulator of protease activity HflC, stomatin/prohibitin superfamily, whose function is unknown; however, it was proposed that through this domain, proteins can interact with the cell membrane and initiate signaling (Christie et al., *Mol Cell Biol* 31:3845-56, 2011). The MbO1_03198 protein was also selected for further characterization. A domain search for MbO1_03198 identified the diacylglycerol kinase family enzyme motif involved in lipid transport and metabolism, and domains of transcriptional regulator XRE-family helix-turn-helix and transcription elongation factor GreA/GreB, C-term.

The PhoY1 gene is ubiquitously present in virtually every bacterial species, including *M. tuberculosis*. PhoY1 encodes the phosphate-specific transport system accessory protein PhoU involved in regulation of phosphate uptake. Evidence suggests that two putative orthologs of PhoU, PhoY1 and PhoY2, promote *M. tuberculosis* persistence phenotype by Pst-mediated phosphate sensing and enhance increased resistance to antibiotics both in vitro and in mice (Shi and Zhang, *J Antimicrob Chemother* 65:1237-1242, 2010; Namugenyi et al., *MBio* 8(4):e00494-17, 2017). In a study addressing the *M. tuberculosis* response to several stress conditions, PhoU was found to have a major role in maintaining metabolic homeostasis and adaptation to stress conditions (Wang et al., *J Bacteriol* 195:243-252, 2013), also offering possible explanation for PhoU related drug tolerance. It is demonstrated herein that phoY1 overexpression on the surface of *M. bovis* helps bacteria to better bind and invade epithelia cells and MDBK cells.

The heparin-binding hemagglutinin (hbhA) protein is a well-studied virulence factor of *M. tuberculosis, M. avium* and *M. leprae*, and plays a crucial role in bacterial binding to epithelial cells and to other non-phagocytic cells (Pethe et al, *Nature* 412:190-194, 2001; Silva et al., *Infect Immun* 81:2645-2659, 2013; Lefrancois et al., *BMC Res Notes* 6:55, 2013). It has been demonstrated that hbhA is involved in extrapulmonary dissemination during tuberculosis infection and in the binding of *M. leprae* to the respiratory mucosa (Pethe et al., *Nature* 412:190-194, 2001; Silva et al., *Infect Immun* 81:2645-2659, 2013; Lanfranconi and Alvarez, *Biochimie* 127:241-248, 2016). Mucosal immunization with the yeast-expressed recombinant hbhA impairs extrapulmonary dissemination of *M. bovis* BCG and, in combination with a mucosal adjuvant, hbhA induces immune protection against mycobacterial infection by triggering systemic and local humoral immunity (Kohama et al., *Vaccine* 26:924-932, 2008). Although hbhA was present in both phenotypes of granuloma-like and regular lab condition of *M. bovis* BCG, because of the potential function and effect on the immune response, this protein was selected for analysis and its function in binding and invasion of human epithelial cells and bovine MDBK cells was confirmed.

In the present study, Mb1524, MbO1_03198, phoY1_1 and hbhA were further investigated in vivo for immunization antigenicity. The results indicate that while all *M. smegmatis* clones overexpressing proteins did not improve the immune antibody response for either IgA or IgG, recombinant protein delivery by either intranasal immunization or intraperitoneal injection stimulated specific IgA and IgG antibody levels, and total IgA and IgG were increased following IP immunization. It is well established that the increased levels of IgA and IgG expressly influence the mucosal immune response and protect the host from *M. bovis* BCG infection. Significant changes in bacterial burden in the lungs were observed in mice that received the mixture of recombinant proteins by the intranasal immunization.

Taken together, the results disclosed herein indicate improved protective efficacy of the recombinant protein mixture of Mb1524, MbO1_03 198, phoY1_1 and hbhA against *M. Bovis* BCG at the mucosal surface.

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

The invention claimed is:

1. An immunogenic composition, comprising at least four isolated surface proteins from *Mycobacterium bovis*, wherein the at least four isolated surface proteins comprise:

a protein comprising at least 90% sequence identity with the amino acid sequence of SEQ ID NO: 2;

a protein comprising at least 90% sequence identity with the amino acid sequence of SEQ ID NO: 4;

a protein comprising at least 90% sequence identity with the amino acid sequence of SEQ ID NO: 6; and a protein comprising at least 90% sequence identity with the amino acid sequence of SEQ ID NO: 8, wherein the immunogenic composition is formulated for mucosal administration, intranasal administration or intramuscular administration.

2. The immunogenic composition of claim 1, wherein the at least four isolated surface proteins from *M. bovis* comprise:

a protein comprising at least 95% sequence identity with the amino acid sequence of SEQ ID NO: 2;

a protein comprising at least 95% sequence identity with the amino acid sequence of SEQ ID NO: 4;

a protein comprising at least 95% sequence identity with the amino acid sequence of SEQ ID NO: 6; and a protein comprising at least 95% sequence identity with the amino acid sequence of SEQ ID NO: 8.

3. The immunogenic composition of claim 1, wherein the at least four isolated surface proteins from *M. bovis* comprise:

a protein comprising the amino acid sequence of SEQ ID NO: 2;

a protein comprising the amino acid sequence of SEQ ID NO: 4;

a protein comprising the amino acid sequence of SEQ ID NO: 6; and a protein comprising the amino acid sequence of SEQ ID NO: 8.

4. A method of eliciting an immune response against *M. bovis* or an *M. bovis* antigen in a subject, comprising intransally or intramuscularly administering to the subject the immunogenic composition of claim 3, thereby eliciting an immune response against *M. bovis* or N *M. bovis* antigen in the subject.

5. The immunogenic composition of claim 1, further comprising a pharmaceutically acceptable carrier, an adjuvant, or both.

6. A method of eliciting an immune response in a subject, comprising administering to the subject the immunogenic composition of claim 1, thereby eliciting an immune response in the subject.

7. The method of claim 6, wherein the immunogenic composition is administered intranasally or intramuscularly.

8. The method of claim 6, wherein the subject is a non-human animal.

9. The method of claim 8, wherein the subject is a bovine subject.

10. A kit comprising the immunogenic composition of claim 1, and instructions for administration of the immunogenic composition and/or a description of the components of the immunogenic composition.

11. The immunogenic composition of claim 1, wherein the immunogenic composition formulated for mucosal administration is formulated for oral, pulmonary, rectal or vaginal administration.

12. An immunogenic composition, comprising:

at least four isolated surface proteins from *Mycobacterium bovis*, wherein the at least four isolated surface proteins comprise a protein comprising at least 90% sequence identity with the amino acid sequence of SEQ ID NO: 2; a protein comprising at least 90% sequence identity with the amino acid sequence of SEQ ID NO: 4; a protein comprising at least 90% sequence identity with the amino acid sequence of SEQ ID NO: 6; and a protein comprising at least 90% sequence identity with the amino acid sequence of SEQ ID NO: 8; and an adjuvant comprising a block polymer, squalene and sorbitan monooleate.

13. The immunogenic composition of claim 12, wherein the at least four isolated surface proteins from *M. bovis* comprise a protein comprising at least 95% sequence identity with the amino acid sequence of SEQ ID NO: 2; a protein comprising at least 95% sequence identity with the amino acid sequence of SEQ ID NO: 4; a protein comprising at least 95% sequence identity with the amino acid sequence of SEQ ID NO: 6; and a protein comprising at least 95% sequence identity with the amino acid sequence of SEQ ID NO: 8.

14. The immunogenic composition of claim 12, wherein the at least four isolated surface proteins from *M. bovis* comprise a protein comprising the amino acid sequence of SEQ ID NO: 2; a protein comprising the amino acid sequence of SEQ ID NO: 4; a protein comprising the amino acid sequence of SEQ ID NO: 6; and a protein comprising the amino acid sequence of SEQ ID NO: 8.

15. The immunogenic composition of claim 12, further comprising a pharmaceutically acceptable carrier.

16. The immunogenic composition of claim 12, wherein the immunogenic composition is formulated for mucosal administration, intranasal administration or intramuscular administration.

17. The immunogenic composition of claim 16, wherein the immunogenic composition formulated for mucosal administration is formulated for oral, pulmonary, rectal or vaginal administration.

18. A kit comprising the immunogenic composition of claim 12, and instructions for administration of the immunogenic composition and/or a description of the components of the immunogenic composition.

* * * * *